(12) United States Patent
Sarel

(10) Patent No.: US 8,043,224 B2
(45) Date of Patent: Oct. 25, 2011

(54) TELEMEDICINE SYSTEM

(75) Inventor: Oded Sarel, Even Yehuda (IL)

(73) Assignee: DiMicine Research IT, LLC, Wilmington, DE (US)

( * ) Notice: Subject to any disclaimer, the term of this patent is extended or adjusted under 35 U.S.C. 154(b) by 753 days.

(21) Appl. No.: 11/390,301

(22) Filed: Mar. 28, 2006

(65) Prior Publication Data

US 2006/0167346 A1 Jul. 27, 2006

Related U.S. Application Data

(60) Continuation-in-part of application No. 10/955,004, filed on Sep. 30, 2004, which is a continuation-in-part of application No. 10/262,874, filed on Oct. 3, 2002, now Pat. No. 6,949,073, application No. 11/390,301, which is a continuation-in-part of application No. 10/608,336, filed on Jun. 30, 2003, now Pat. No. 7,237,205, which is a division of application No. 09/614,546, filed on Jul. 12, 2000, now abandoned.

(51) Int. Cl.
*A61B 5/08* (2006.01)

(52) U.S. Cl. ........................................................ 600/529

(58) Field of Classification Search ................... 600/529
See application file for complete search history.

(56) References Cited

U.S. PATENT DOCUMENTS

| | | |
|---|---|---|
| 3,688,413 A | 9/1972 | Harte |
| 3,786,510 A | 1/1974 | Hodges |
| RE28,513 E | 8/1975 | Suzuki et al. |
| 4,216,462 A | 8/1980 | McGrath et al. |
| 4,284,847 A | 8/1981 | Besserman |
| 4,351,344 A | 9/1982 | Stenzler |
| 4,367,752 A | 1/1983 | Jimenez et al. |
| 4,489,610 A | 12/1984 | Slavin |
| 4,561,449 A | 12/1985 | Hu et al. |
| 4,573,050 A | 2/1986 | Waters |
| 4,671,772 A | 6/1987 | Slade et al. |
| 4,740,072 A | 4/1988 | Griffin et al. |
| 4,768,074 A | 8/1988 | Yoshida et al. |
| 4,803,625 A | 2/1989 | Fu et al. |
| 5,002,055 A | 3/1991 | Merki et al. |
| 5,002,491 A | 3/1991 | Abrahamson et al. |
| 5,008,853 A | 4/1991 | Bly et al. |
| 5,019,974 A | 5/1991 | Beckers |
| 5,088,981 A | 2/1992 | Howson et al. |

(Continued)

FOREIGN PATENT DOCUMENTS

EP 0251520 1/1988

(Continued)

OTHER PUBLICATIONS

Cho et al. "Adaptive Antennas Employing Vertical Pattern Control for Street Microcell", IEEE, NY, p. 639-642, 1998. p. 642, Fig.7; Claims: 4-6.

(Continued)

*Primary Examiner* — Patricia Mallari
(74) *Attorney, Agent, or Firm* — Knobbe, Martens, Olson & Bear, LLP

(57) ABSTRACT

System for remote medical interaction with a patient, comprising: a tester, or a sensor, for acquiring medical data from a patient and a personal transmitter, associated with the tester, or a sensor, configured to automatically and wirelessly transmit the medical data.

29 Claims, 15 Drawing Sheets

U.S. PATENT DOCUMENTS

| | | |
|---|---|---|
| 5,103,408 A | 4/1992 | Greenberg et al. |
| 5,165,417 A | 11/1992 | Murphy, Jr. |
| 5,197,332 A | 3/1993 | Shennib |
| 5,211,564 A | 5/1993 | Martinez et al. |
| 5,262,944 A | 11/1993 | Weisner et al. |
| 5,267,865 A | 12/1993 | Lee et al. |
| 5,283,856 A | 2/1994 | Gross et al. |
| 5,298,021 A | 3/1994 | Sherer |
| 5,306,154 A | 4/1994 | Ujita et al. |
| 5,310,349 A | 5/1994 | Daniels et al. |
| 5,375,199 A | 12/1994 | Harrow et al. |
| 5,422,690 A | 6/1995 | Rothberg et al. |
| 5,437,055 A | 7/1995 | Wheatley |
| 5,451,162 A | 9/1995 | Parsons |
| 5,473,537 A | 12/1995 | Glazer et al. |
| 5,486,835 A | 1/1996 | Hock |
| 5,517,405 A | 5/1996 | McAndrew et al. |
| 5,520,192 A | 5/1996 | Kitney et al. |
| 5,542,420 A | 8/1996 | Goldman et al. |
| 5,549,117 A | 8/1996 | Tacklind et al. |
| 5,553,609 A | 9/1996 | Chen et al. |
| 5,609,827 A | 3/1997 | Russell et al. |
| 5,619,991 A | 4/1997 | Sloane |
| 5,623,598 A | 4/1997 | Voigt et al. |
| 5,647,834 A | 7/1997 | Ron |
| 5,677,979 A | 10/1997 | Squicciarini et al. |
| 5,680,560 A | 10/1997 | Gaertner |
| 5,686,926 A | 11/1997 | Kijimia et al. |
| 5,715,823 A | 2/1998 | Wood et al. |
| 5,758,652 A | 6/1998 | Nikolic |
| 5,765,563 A | 6/1998 | Vander Schaaf |
| 5,769,074 A | 6/1998 | Barnhill et al. |
| 5,791,342 A | 8/1998 | Woodard |
| 5,791,908 A | 8/1998 | Gillio |
| 5,801,755 A | 9/1998 | Echerer |
| 5,810,747 A | 9/1998 | Brundy et al. |
| 5,811,681 A | 9/1998 | Braun et al. |
| 5,827,180 A | 10/1998 | Goodman |
| 5,840,018 A | 11/1998 | Michaeli |
| 5,842,975 A | 12/1998 | Illyes et al. |
| 5,842,977 A | 12/1998 | Lesho et al. |
| 5,848,975 A | 12/1998 | Phillips |
| 5,851,186 A | 12/1998 | Wood et al. |
| 5,855,550 A | 1/1999 | Lai et al. |
| 5,859,972 A | 1/1999 | Subramaniam et al. |
| 5,865,733 A | 2/1999 | Malinouskas et al. |
| 5,868,134 A | 2/1999 | Sugiyama et al. |
| 5,868,135 A | 2/1999 | Kaufman et al. |
| 5,868,669 A | 2/1999 | Iliff |
| 5,873,369 A | 2/1999 | Laniado et al. |
| 5,879,292 A | 3/1999 | Sternberg et al. |
| 5,891,185 A * | 4/1999 | Freed et al. ............... 607/72 |
| 5,892,570 A | 4/1999 | Stevens |
| 5,895,345 A | 4/1999 | Knelson |
| 5,895,354 A | 4/1999 | Simmons |
| 5,897,493 A | 4/1999 | Brown |
| 5,902,234 A | 5/1999 | Webb |
| 5,906,208 A | 5/1999 | Ishikawa et al. |
| 5,907,291 A | 5/1999 | Chen et al. |
| 5,928,160 A | 7/1999 | Clark et al. |
| 5,931,160 A | 8/1999 | Gilmore et al. |
| 5,961,446 A | 10/1999 | Beller et al. |
| 5,961,447 A | 10/1999 | Raviv et al. |
| 5,978,292 A | 11/1999 | Lim |
| 6,016,123 A | 1/2000 | Barton et al. |
| 6,022,315 A | 2/2000 | Iliff |
| 6,073,046 A | 6/2000 | Patel et al. |
| 6,080,106 A | 6/2000 | Lloyd et al. |
| 6,094,166 A | 7/2000 | Martek et al. |
| 6,104,343 A | 8/2000 | Brookner et al. |
| 6,113,540 A | 9/2000 | Illiff |
| 6,135,951 A | 10/2000 | Richardson et al. |
| 6,168,563 B1 | 1/2001 | Brown |
| 6,168,568 B1 | 1/2001 | Gavriely |
| 6,178,333 B1 | 1/2001 | Feuerstein et al. |
| 6,181,276 B1 | 1/2001 | Schlekewey et al. |
| 6,206,829 B1 | 3/2001 | Iliff |
| 6,222,544 B1 | 4/2001 | Tarr et al. |
| 6,241,683 B1 | 6/2001 | Macklem et al. |
| 6,289,244 B1 | 9/2001 | Conley et al. |
| 6,295,506 B1 | 9/2001 | Heinonen et al. |
| 6,302,844 B1 | 10/2001 | Walker et al. |
| 6,308,102 B1 | 10/2001 | Sieracki et al. |
| 6,320,585 B1 | 11/2001 | Engel et al. |
| 6,322,502 B1 | 11/2001 | Schoenberg et al. |
| 6,364,834 B1 | 4/2002 | Reuss et al. |
| 6,369,838 B1 | 4/2002 | Wallace et al. |
| 6,406,426 B1 | 6/2002 | Reuss |
| 6,504,517 B1 | 1/2003 | Liu et al. |
| 6,648,820 B1 | 11/2003 | Sarel |
| 6,949,073 B2 | 9/2005 | Sarel |
| 2001/0034717 A1 | 10/2001 | Whitworth |
| 2001/0047125 A1* | 11/2001 | Quy ............... 600/300 |
| 2002/0082480 A1 | 6/2002 | Riff et al. |
| 2002/0138306 A1 | 9/2002 | Sabovich |
| 2003/0062045 A1 | 4/2003 | Woodring et al. |
| 2004/0008219 A1 | 1/2004 | Sarel |
| 2004/0015056 A1 | 1/2004 | Shinoda |
| 2004/0063467 A1 | 4/2004 | Shapira et al. |
| 2004/0068197 A1 | 4/2004 | Sarel |
| 2004/0111040 A1* | 6/2004 | Ni et al. ............... 600/534 |
| 2005/0043969 A1 | 2/2005 | Sarel |
| 2005/0060187 A1 | 3/2005 | Gottesman |
| 2005/0085738 A1* | 4/2005 | Stahmann et al. ............ 600/529 |
| 2006/0167346 A1 | 7/2006 | Sarel |
| 2006/0276718 A1 | 12/2006 | Madaus et al. |

FOREIGN PATENT DOCUMENTS

| | | |
|---|---|---|
| EP | 1014485 | 6/2000 |
| IL | 105547 | 10/1996 |
| WO | WO 98/02083 | 1/1998 |
| WO | 01/30231 | 5/2001 |
| WO | WO 02/061878 | 8/2002 |
| WO | WO 2004/030509 | 4/2004 |
| WO | WO 2005/0123109 * | 3/2005 |

OTHER PUBLICATIONS

Microsoft Microsoft Screen Captures, Windows Version 4.0, Figs.1-11, 1981-1998.

BACS AVAT Model 201: Automated Self-Operated Vision Tester, pp. 1-2.

"The health.net Industry—The Convergence of Healthcare and the Internet," Jan. 8, 1999, pp. 1-38, Fitzgibbons, Stephen et al.

BACS Profile: Revolutionizing Medical Data Collection & Management, pp. 1-2.

BACS Automated Self Operated Audiometer, Model 101 (Product Description), pp. 1-2.

Panasonic Vital Signs Box (Product Description), Matsushita Electric Industrial Co., Ltd., p. 1, Dec. 6, 1999.

http://www.schiller.ch/about.htm, (web page) Oct. 25, 1999.

International Search Report from PCT/IL00/000678, dated Jul. 9, 2001.

International Search Report from PCT/IL03/000793, dated Apr. 29, 2004.

* cited by examiner

Welcome to your online checkup
for 11/6/01

1. Login     Name     [          ]
             Password [          ]

Fig. 9

Hello Mr Smith

Please answer the following questions

1. How do you feel today?

Fine ◎   OK ◎   Lousy ◎   Nauseous ◎   Terrible ◎

2. Have you taken this morning's tablets?

Yes     No

Fig. 10

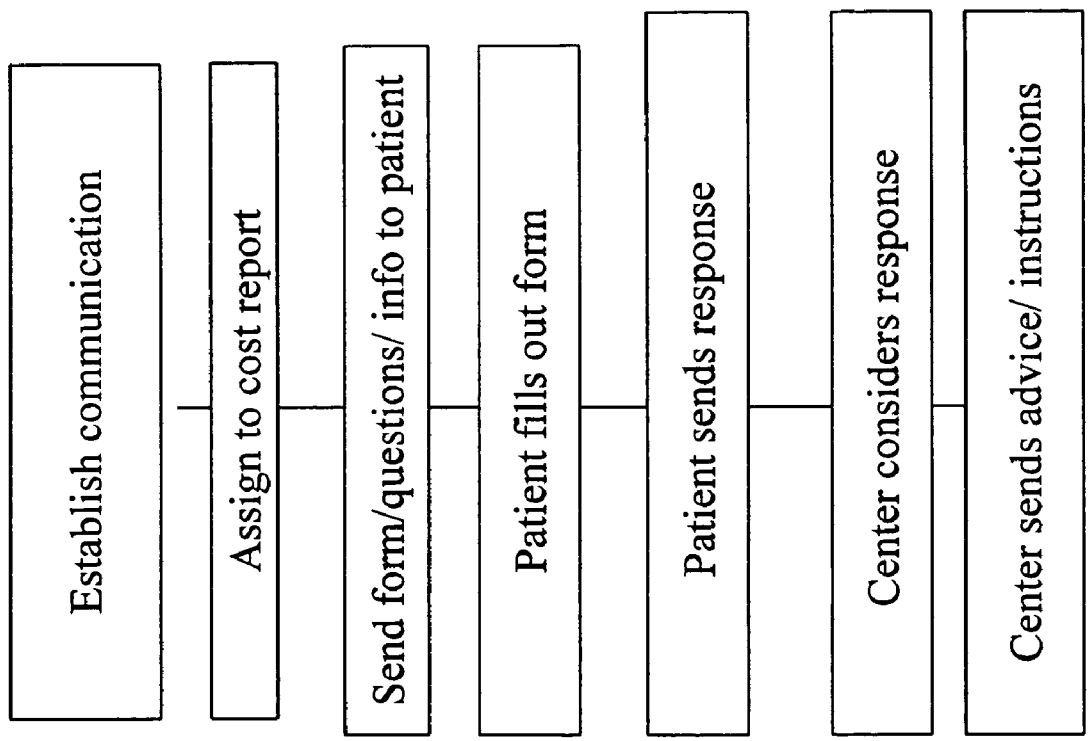

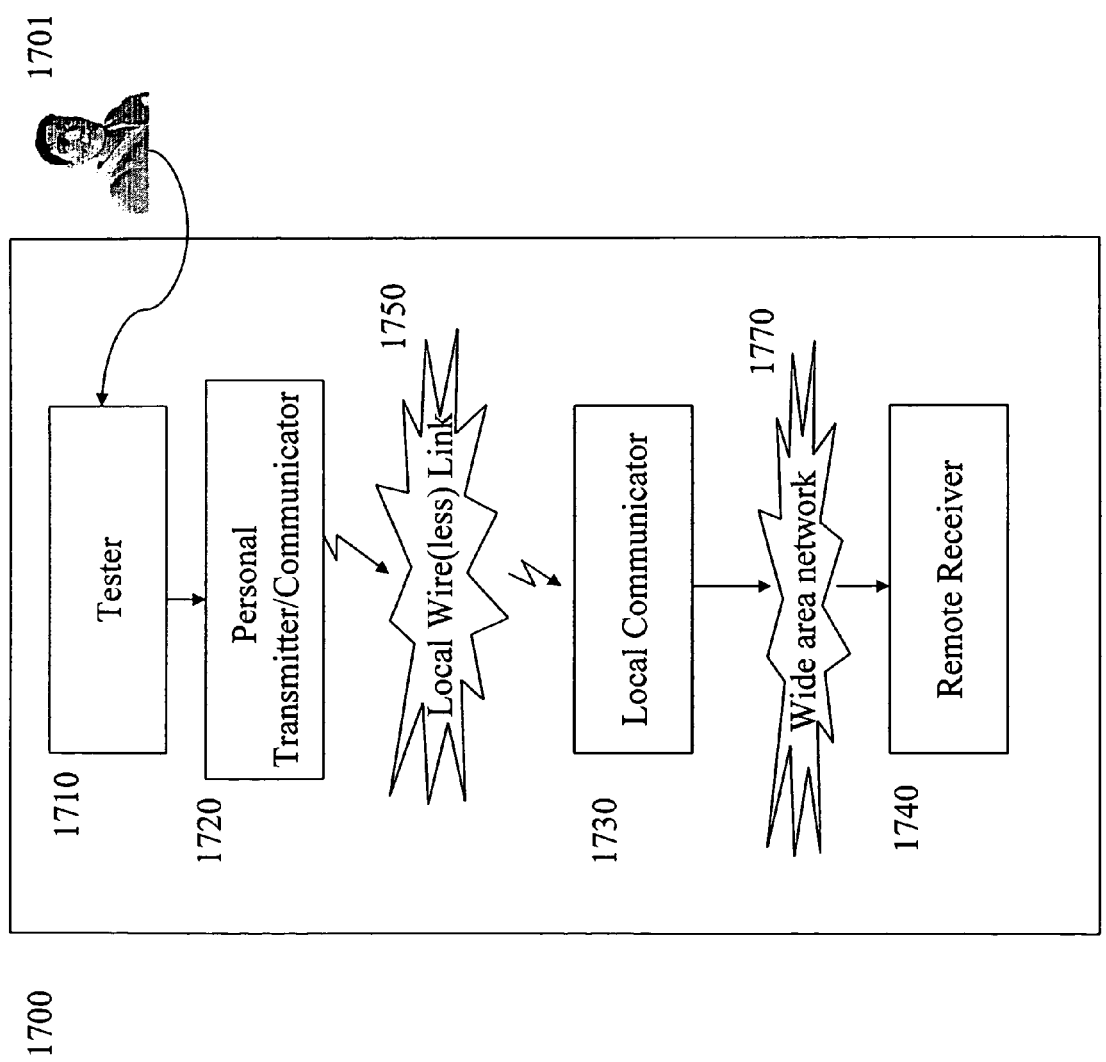

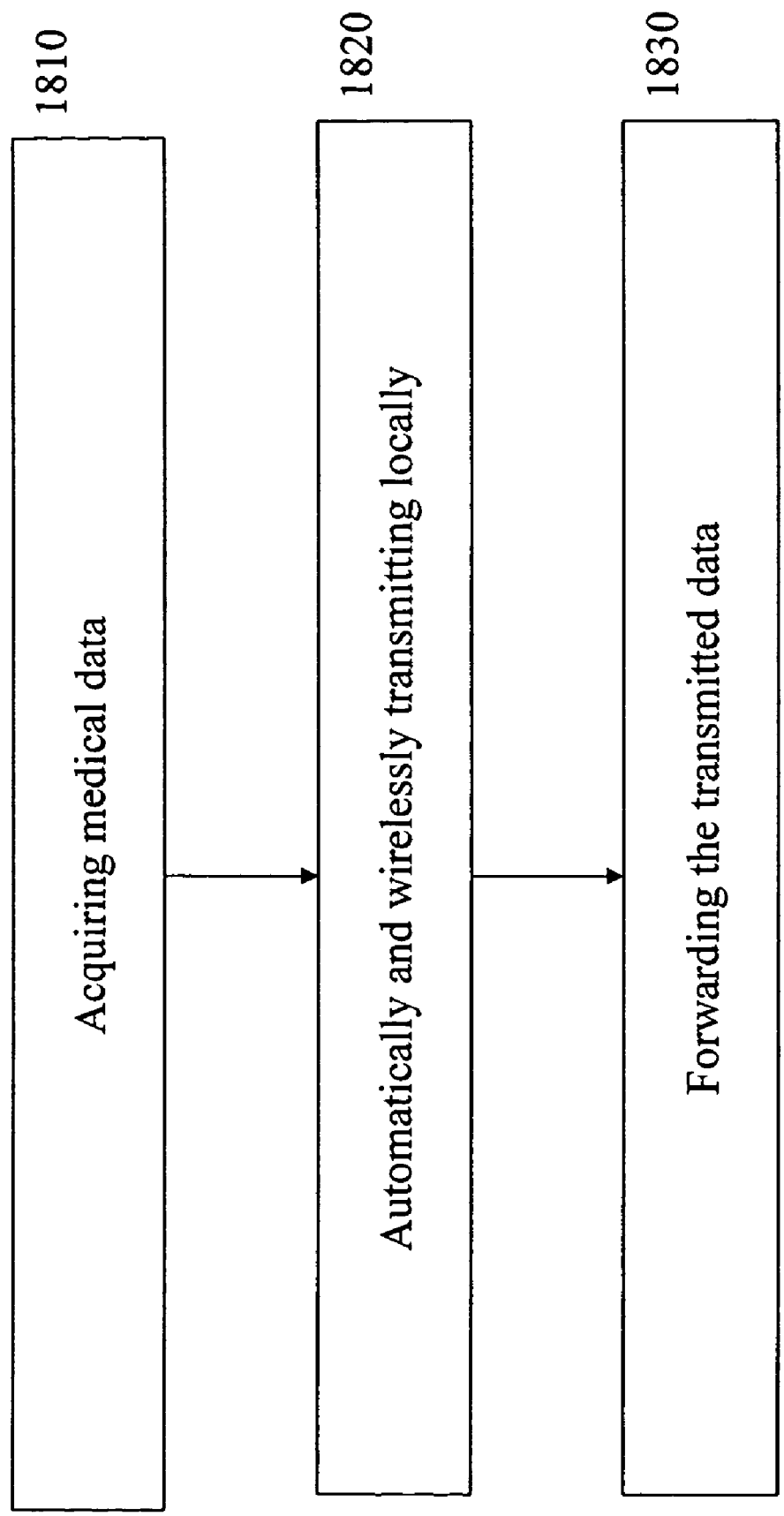

TELEMEDICINE SYSTEM

RELATED APPLICATIONS

This application is a continuation-in-part of pending U.S. patent application Ser. No. 10/955,004, filed on Sep. 30, 2004, which is a continuation-in-part of U.S. patent application Ser. No. 10/262,874, filed on Oct. 3, 2002, now U.S. Pat. No. 6,949,073, issued on Sep. 27, 2005.

This application is also a continuation-in-part of pending U.S. patent application Ser. No. 10/608,336, filed on Jun. 30, 2003, which is a divisional of U.S. patent application Ser. No. 09/614,546, filed on Jul. 12, 2000, now abandoned.

The contents of the above applications are all incorporated herein by reference.

FIELD AND BACKGROUND OF THE INVENTION

The present invention relates to a telemedicine system for communication with remotely located patients, and more particularly but not exclusively to a system for remote communication of patient self administrated tests. Telemedicine systems provide an opportunity for home monitoring of post-operative patients, for preventative medicine where the burden on the health infrastructure of carrying out wide scale monitoring would be prohibitive, for reducing the time spent in hospital, for making patients more independent etc. Wherever there is a test that can be carried out automatically or manually self-administered by the patient, then telemedicine can be used to ensure that the results are obtained in a competent way and dealt with responsibly.

An example of an opportunity for telemedicine is in cases where symptoms show themselves in the respiratory system. A number of respiratory problems are preceded by detectable reductions in the ability to inhale or hold one's breath. Thus, it is possible to determine from a simple breathing test whether a patient is likely to suffer from such problems in the short term. Such a simple test is described in the literature in which the patient is placed in a rest position, asked to take a deep breath and then to count continuously until he has to take a breath again. An unusually short interval between breaths is indicative of congestion of the lungs or breathing passages.

The patient is generally not in the presence of a doctor at the times the test can yield the most helpful information, and indeed, the test is most useful as part of regular and frequent monitoring.

Furthermore the results of the test taken alone may not lead directly to any given diagnosis, the doctor preferring to take the test results in combination with other patient indicators before reaching a diagnosis of any kind.

Generally, automatic decision devices exist but are not widely used in the medical field since it is difficult to determine how decisions have been made and how different factors have been taken into account if at all.

An earlier patent application of the same inventor, WO IL00/00678, filed Oct. 25, 2000, which is hereby incorporated by reference, describes a system in which a plurality of tests can be administered remotely over a telemedicine system, the patient being given instructions to administer the tests and then the test results being considered together to produce recommendations.

The recommendations are then given either to the patient or to the doctor or both. A rule structure is used to lead from results to recommendations in a way that allows for easy checking by the responsible doctor and which avoids masking of bad test results by other better test results. The rule structure is however inadequate for certain given situations.

In the event that the same patient is being monitored by more than one doctor for different reasons or conditions, the above device requires either that the single monitoring device monitors everything and each doctor receives all of the information, or that two separate monitoring instances are used, increasing the inconvenience to the patient.

U.S. Pat. No. 5,772,586, filed on Feb. 4, 1997, entitled "a method for monitoring the heath of a patient", teaches a method for monitoring a patient. However, with this patent the patient has to wire a medical testing device into a telephony network device, connected to a public telephony network, for transmitting medical (health) data.

Other patents relating to telemedicine include: U.S. Pat. Nos. 5,907,291; 5,906,208; 5,902,234; 5,897,493; 5,895,354; 5,892,570; 5,879,292; 5,873,369; 5,868,669; 5,868,135; 5,868,134; 5,865,733; 5,855,550; 5,848,975; 5,842,977; 5,842,975; 5,840,018; 5,827,180; 5,811,681; 5,791,908; 5,791,342; 5,769,074; 5,758,652; 5,677,979; 5,619,991.

There is thus a widely recognized need for, and it would be highly advantageous to have a telemedicine system which is devoid of the above limitations.

SUMMARY OF THE INVENTION

According to one aspect of the present invention there is provided a system for remote medical interaction with a patient, comprising: a tester, or a sensor for acquiring medical (health) data from a patient and a personal transmitter, associated with the tester, or a sensor, configured to automatically and wirelessly transmit the medical (health) data. The tester may include a sensor, a medical sensor, or any other device for measuring a health condition in a patient. Medical (health) data includes any kind of measurable or verbal information from human being. Optionally, the sensor may include processing ability, and programming capabilities The system may further comprise a local communicator, configured to forward the medical (health) data to a remote receiver.

The system may further comprise a remote receiver, configured to receive and process the medical (health) data.

Optionally, the personal transmitter is further configured to use wireless communication abilities, including radio waves, Bluetooth—Short range radio links in the 2.4 GHZ frequency range, WiMax—Broadband wireless networks that are based on the IEEE 802.16 standard, Wireless Fidelity (WiFi)—wireless local area networks (WLAN) that use specifications conforming to IEEE 802.11b, etc. for transmitting the medical data.

Optionally, the tester, or a sensor, the local communicator, or the remote communicator comprises: a breathing interval beginning determinator, for determining a beginning of a breathing interval, a breathing interval end determinator, for determining a termination of the breathing interval, a timer associated with the breathing interval beginning determinator and the breathing interval end determinator to measure a time interval between the beginning and the determination, and a processor operable with the timer to assign levels of importance to the measured time interval.

Optionally, the processor is further configured to compare the time interval with at least one threshold, for assigning the levels of importance.

In one example, an ischemic disease patient may be provided with a medical sensor and a personal transmitter which wirelessly and continuously transmits cardiac medical (health) data to a medical center, say through a local communicator as described herein below.

The continuous monitoring of the ischemic patient in real time facilitates immediate detection of an ischemic emergency condition such as a heart attack or a state of severe arrhythmia, say according to a rapidly elevating blood pressure, an accelerated heart rate, or any other relevant indicator (s) present in the cardiac medical (health) data.

The real time delivery of medical (health) data to the medical center may prove life saving as the sooner a stressed patient is treated, to more likely he is to survive an heart attack or any other medical emergency situation.

Unless otherwise defined, all technical and scientific terms used herein have the same meaning as commonly understood by one of ordinary skill in the art to which this invention belongs. The materials, methods, and examples provided herein are illustrative only and not intended to be limiting.

Use of the term General Purpose Computer includes any device having digital processing capabilities including but not limited to desktop computers, laptop computers, personal digital assistants, mobile and cordless handsets and hybrids thereof Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 9, 10 and 11 are simplified diagrams showing possible user screens of a web implementation of the present invention, FIG. 9 showing a login page, FIG. 10 showing some introductory questions and FIG. 11 showing instructions for carrying out the breathing test of FIG. 1.

FIG. 16 is a simplified diagram illustrating an ERM based procedure using the infrastructure of FIG. 12.

FIG. 17*a* is a simplified block diagram illustrating a first system for remote medical interaction with a patient, according to a preferred embodiment of the present invention.

FIG. 18 is a flowchart illustrating a method for remote medical interaction with a patient, according to a preferred embodiment of the present invention.

DESCRIPTION OF THE PREFERRED EMBODIMENTS

Figure 1:
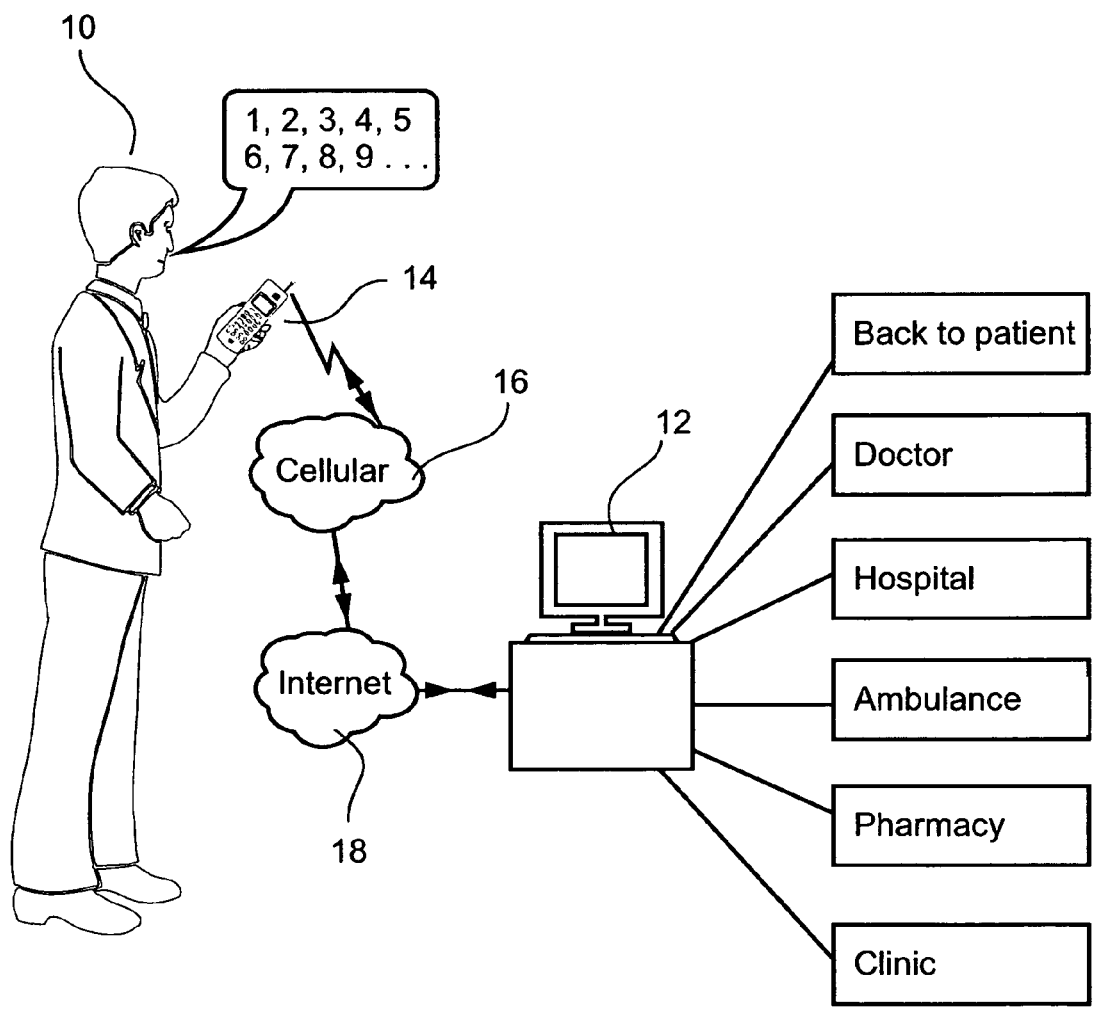
FIG. 1 is a simplified block diagram showing a subject undergoing breathing monitoring under control of a remote monitoring system according to a first embodiment of the present invention.

The present embodiments comprise a system for remote medical interaction with a patient.

The principles and operation of a system according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which is a simplified schematic diagram showing a first embodiment of the present invention. In the embodiment of FIG. 1 a patient or subject 10 contacts a remote monitoring unit 12 using a remote communication device such as a mobile telephone 14.

It will be appreciated that any remote communication device may be considered including regular telephones, digital assistants, and Internet connected portable and other computers.

It will also be appreciated that any available communication medium or network may be used, including the traditional telephone networks (PSTN), cellular telephone networks, cable TV networks, Worldwide Interoperability for Microwave access (WiMax) networks—Broadband wireless networks that are based on the IEEE 802.16 standard, Bluetooth—Short range radio links in the 2.4 GHZ frequency range, WiFi—wireless local area networks (WLAN) that use specifications conforming to IEEE 802.1b, standard radio channels, or any other radio wave channel.

Devices having some ability to allow digital communication are preferred for some embodiments of the present invention, and devices having a digital processing ability may provide some or all of the processing to be described hereinbelow of input measurements.

The remote communication device preferably connects to the monitoring unit 12 using any suitable network, for example the cellular network 16 and the Internet 18. It is stressed again that other alternatives include but is not limited to the PSTN, WiFi, WiMax, Bluetooth, radio links, cable connections, and messaging services such as SMS.

The remote monitoring device 12 preferably asks the subject 10 to identify himself and then gives him instructions to carry out a particular monitoring or measurement procedure. The subject 10 is preferably told how to make the measurement and how to send the result to the monitoring unit 12.

In FIG. 1, the monitoring unit is denoted as a remote monitoring unit and is shown at the hospital side of the network connection. However, that is simply by way of example and the processing task carried out by the monitoring unit may be carried out at any convenient point between the patient and the medical professional. Typically, when the patient connects using a digital device the various processing tasks may be carried out at the user or split between the user and a remote unit. In other embodiments the user connects manually over a telephone, in which case processing is typically carried out remotely of the patient.

The monitoring unit preferably assesses the result, as will be explained in more detail below, to come to a recommendation or decision. The recommendation is then communicated either back to the patient, or to the doctor in charge of the treatment or to the hospital or to a pharmacy if a repeat prescription is needed, or to a clinic or, in the event of an emergency, the ambulance is contacted. Typical recommendations may be to stop treatment, change treatment, continue as before, see the doctor, go immediately to the hospital, etc.

In a preferred embodiment of the present invention the remote monitor 12 serves as a dyspnea monitor for monitoring the intervals of a subject's breathing, typically to ensure that he is not suffering from constrictions or pneumonia or fluid in the lung or other breathing constrictions. Such monitoring is useful in giving advance warning of given conditions to allow early treatment.

When in use as a dyspnea monitor the subject is requested to relax and then inhale. The subject is then asked to breathe out slowly or to count or to speak normally and the remote monitor times the interval until the next intake of breath. The measurement may be taken once or several times and an average determined The remote monitor 12 is able to assign a status or level of importance to the result, such as red, amber, green. The status may be communicated back to the patient or may be communicated to the doctor etc. or may be combined with other results, thereby to provide more comprehensive monitoring of the patient. As will be explained in more detail below, the result may be interpreted in the light of a patient's known medical history so that, for example, results that in most cases would elicit only a green status may be given a red or amber status in the light of the appearance of a given condition in the patient's medical history.

As an alternative to red, amber, green, a preferred embodiment uses the five states 0, 1, 2, alert and emergency. In this case, alert may be a state calling for a medical professional to visit the patient whereas emergency may be a state calling the patient to head immediately for casualty. Alternatively, an alert state may send an e-mail whereas an emergency state may send a voice alert.

It will be appreciated that, as well as being used in association with remote communication, the monitoring device may be used alone, either for later connection to remote communication or simply to report results directly to the patient.

Figure 2:
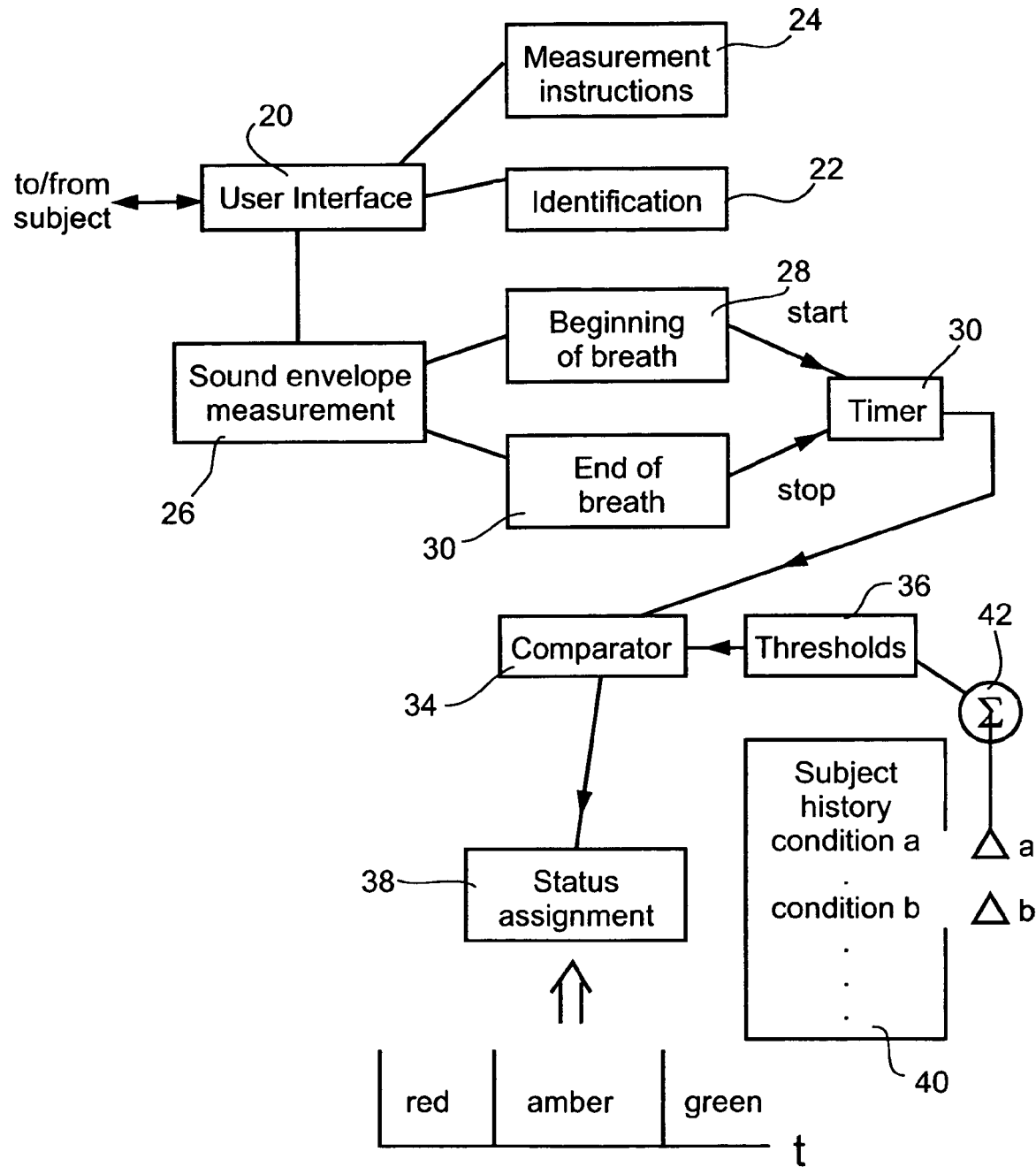
FIG. 2 is a simplified block diagram of the monitoring system of FIG. 1.

Reference is now made to FIG. 2, which is a simplified block diagram showing in more detail the monitoring apparatus of FIG. 1 configured as a dyspnea monitor, that is to say as a breathing interval measurement apparatus. The apparatus is useful for measuring breathing of a subject.

Remote monitor 12 comprises a user interface 20 for interfacing with the subject 10. The interface 20 is preferably designed to be suitable for the remote communication device being used by the user 10. That is to say if the remote communication device is a WAP-enabled mobile telephone then the interface preferably uses a WAP-compatible front end. If the remote communication device is an internet enabled desktop or mobile computer then the interface may for example make use of a web-page construction as a front end.

Preferably the user interface 20 allows the subject to enter an identification procedure 22. The identification procedure preferably asks the subject to give a name and perhaps a password. Identification is preferred for a number of reasons. First of all, as will be explained below, the subject may need to be associated with his own medical history in order to provide suitable decision making. Furthermore the results of the monitoring may need to be supplied to the doctor who is treating the particular subject. More generally the monitoring device is not intended as a freely available computerized doctor but rather as a tool to assist doctors in patient treatment. As such the addition of an identification procedure restricts use of the monitoring device to those patients whose doctors feel it will be beneficial and who are monitoring particular conditions and combinations of conditions.

An alternative identification procedure may make use of voiceprint or other personal identification technology.

In addition to the identification procedure the interface is also provided with sets of instructions 24 for advising the subject or patient on how to carry out given procedures. For example in the case of the dyspnea monitor, the user may be asked to sit down in a comfortable position and to relax. He is invited to indicate that he is relaxed by pressing on a given key. He is then asked to take a deep breath and begin counting. Suitable instruction sets may be made available for a wide variety of monitoring or measurement procedures and may be selected in accordance with a patient profile obtained following identification of the subject.

In the case of the dyspnea monitor the user preferably speaks a given sentence or counts or the like. The sentence is monitored, preferably at the remote monitoring unit 12, by a sound intensity envelope measurement unit 26. The sound intensity envelope measurement unit 26 produces a sound intensity envelope from which a beginning of exhalation may be identified by a breath beginning identifier 28. An output of the breath beginning identifier 28 is preferably used to trigger a timer 30 to start timing.

Likewise a second beginning of inhalation detector 32 is able to determine the end of the exhalation from the measured sound envelope. An output of the exhalation end detector is preferably used to stop the timer 30 so as to leave as an output of the timer an interval indicating the length of exhalation. The output may be used as it is or an average may be calculated from several measurements. The system may be set to ignore results in which exhalation was reduced in duration due to a subject coughing. On the other hand the system may be set to record such results as they may be of interest to the doctor.

Thus the output of the timer is either passed directly to a comparator 34 or the computed average or another statistical derivative of the timer output(s) is passed to the comparator 34. The comparator compares the result with a set of thresholds stored in a thresholder 36 and assigns a status or level of importance to the output at a status assigner 38, depending on where the result falls between the thresholds.

Preferably the identification procedure has allowed a subject profile 40 to be found. The subject profile preferably includes pertinent medical history of the subject including conditions that the subject is known to be suffering from. Generally speaking, the conditions that a user suffers from modify the levels of importance that should be attached to given measurements. For example a TB or an AIDS patient may require immediate treatment in the case of relatively minor restriction of the airways since such conditions are consistent with rapid development of airway constriction. A patient not suffering from the above conditions, on the other hand, may not require any kind of treatment at all when showing the same level of constriction. Other examples of patients requiring treatment include congestive heart failure and bronchial asthma.

Preferably, the above situation is dealt with by providing with each condition a set of deltas to be applied to the thresholds of individual measurements. Thus the TB condition may have a large delta to be applied to breathing interval thresholds, whereas it may have a smaller or zero delta for heart rate measurements. The AIDS condition may also have a large delta for breathing interval thresholds and preferably the device sums the different deltas of the conditions that are present in a summing unit 42 and moves the thresholds according to the summed output of the deltas. It will thus be appreciated that when a subject is suffering from both TB and AIDS, even a very slight change in exhalation time is liable to attain dire warnings from the system.

Status assignment is preferably made in a visually clearly understood manner, for example using the traffic light colors, red, amber and green. Additional states may be added, and existing states may be split into high and low states of the same color. Examples are high and low amber, high and low red, and a purple state. Visual clarity is helpful in allowing the doctor to understand easily how a given recommendation has been reached. Generally, prior art decision making systems have been rejected by the medical profession on the grounds that it has not been possible to investigate recommendations, for example to ensure that all factors have been taken into account. Reference numeral 44 refers to a graph showing measured exhalation time and showing a red region for the shortest breaths, an amber region for breaths of intermediate length and a green region for breaths of normal healthy length. Thus the monitor is operable to assign high levels of importance to short measured intervals and successively lower levels of importance to successively longer intervals.

In certain embodiments, the boundaries between the levels, initially the thresholds as prestored in thresholder 36, may be set universally, to be altered by the deltas of the patient's recorded conditions as described above. In other embodiments, the thresholds may be set by the doctor responsible for the given treatment in view of the patient's history without the option or the need for the modification by the deltas. In still other embodiments the doctor may set the thresholds on an individual basis but allow for modification by the deltas, either all deltas or only those of new conditions as they appear in the patient.

Likewise, deltas may be universally set for given conditions or may be set individually in the patient's medical profile.

In an alternative embodiment of the above, instead of using an automatic beginning of exhalation detector 28, the user is asked to press a key at the beginning of his exhalation, the press of the key being used to trigger the timer 30. In a further simplified embodiment the user is asked to press the same or another key in order to indicate the end of the exhalation, the second key press being used to stop the timer.

Figure 3:
FIG. 3 is a simplified schematic diagram showing the division of a results space into status zones.

Reference is now made to FIG. 3, which is a simplified schematic diagram showing status zones that may be applied by the status assigner 38. In FIG. 3 a series of four zones are applied starting with green at one end, passing through low amber, high amber and red. Such a series of four status zones is applicable to examples similar to the dyspnea monitor in which one safe and one danger area are respectively located at either end of a result range.

Figure 4:
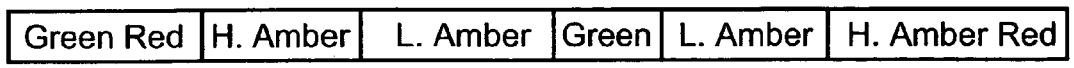
FIG. 4 is a simplified schematic diagram showing the division of a results space into a different arrangement of status zones.

Reference is now made to FIG. 4, which is an alternative embodiment to that of FIG. 3 of a zone distribution. In the example of FIG. 4 a safe zone is found towards the center of the range and danger zones to either side. The result range is thus divided into seven, red, high amber, low amber, green, low amber, high amber, red. A variation of the embodiment of FIG. 4, but less common, has a central red zone and green zones at either end.

It will be appreciated that numerous variations of the above could be used for zoning the results range. For example a single amber zone could be used or three or more different amber zones, or the red zone could be divided into a standard red zone and an emergency red zone.

Figure 5:
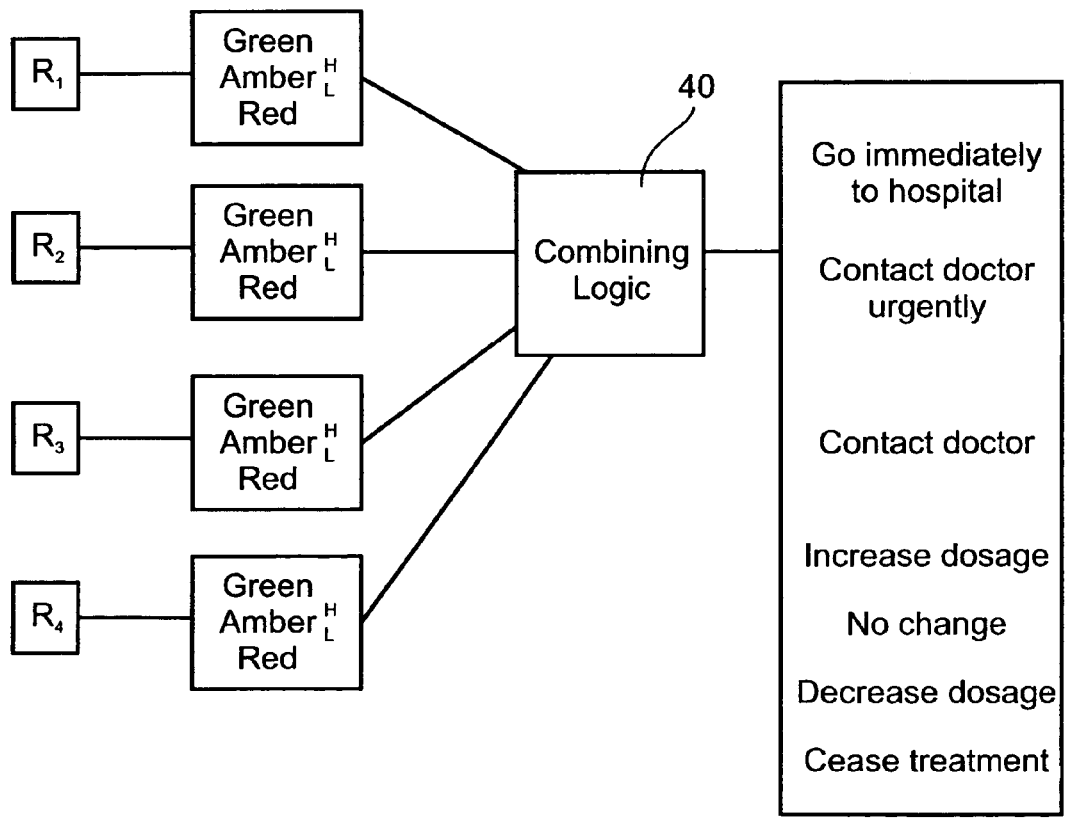
FIG. 5 is a simplified block diagram showing how a series of measurements may be combined into a set of decisions according to an embodiment of the present invention.

Reference is now made to FIG. 5, which is a simplified block diagram showing how a series of measurements from an individual subject may be considered by the present invention. In the embodiment of FIG. 5, a series of results R1 to R4 are obtained from the subject and each result is assigned a status in accordance with a predetermined zoning arrangement which may have been modified using deltas associated with conditions in the patient history, as described above. The output statuses of each of the four measurements are then fed into a combining logic unit 40. The different statuses are considered together to select one of a range 42 of possible output recommendations or decisions. The selection logic 40 preferably uses rules to associate the status combinations with the outputs, as opposed to weightings. A reason for using rules as opposed to weightings is that with weightings, a single bad result can be masked by other good results so that a serious condition may be missed. Using rules for matching allows such a situation to be avoided since a rule can be set to give the output "go directly to hospital" in response to the appearance of any red status in any of the measurements.

The output decisions or recommendations as shown in FIG. 5 may be directed toward the patient, which is to say the recommendation may be worded in layman's terms and sent to the patient as an output response following his submission of the measurements. Additionally or alternatively, however, as shown in FIG. 1, the results may be transferred to other parties, such as the doctor responsible for the patient's treatment. In certain circumstances, such as in post-operative monitoring, different doctors may be responsible for monitoring different problems. Thus it may be possible to direct monitoring results to the different parties as appropriate. For example all results and recommendations relevant to the patient's heart condition are directed to the responsible cardiologist whereas all results and recommendations relevant to the patient's asthmatic condition are directed to another doctor. All information regarding drug treatments is however preferably directed to both doctors.

It is further possible to direct output information on the basis of the recommendation content. For example, if the recommendation "increase dose" is issued, causing the patient to use his supply of pills faster, it may be useful to send a request for a repeat prescription to the pharmacist. Alternatively, in the event of the recommendation "go immediately to hospital" it may be useful to advise the hospital to make facilities available. For example, intensive care or operating facilities or particular surgical staff may be reserved in advance.

Other parties who may be usefully contacted at times may include a laboratory for carrying out a required test, a specialist medical practitioner for providing specialist medical services and a general medical practitioner for providing generalized medical services.

Preferably, interested parties such as the doctor involved in the treatment of the patient's asthma, are able to request the supply of specific data, and he may be able to specify the form in which he requires the data.

The system may be set to report, to the doctor, only messages of relatively high level importance, or alternatively to send to the doctor all output. In the case where the doctor is informed only of recommendations of high level importance, he may nevertheless be able to interrogate the system to obtain a full progress report.

A preferred embodiment of the present invention comprises a modification of the instruction unit 24 of the interface unit. In addition to the instructions for taking the relevant measurement a series of questions are supplied for ensuring that the patient has understood the instructions in the output recommendation. Thus a set of follow-up questions may be associated with each of the possible outputs, which set is selected in the event of the given recommendation being used. The questions are then put to the user, either orally in the case of an audio interface or in written form in the case of a text interface and the user's response is evaluated to determine whether the instructions have been understood. In the event that it appears that the instructions have not been understood the system may for example request medical personnel to contact the subject.

As mentioned above in respect of FIG. 2, user profiles are preferably used in order to take a subject's medical history into account in order to allow thresholds to be modified. The medical history may be input into the system by the subject's doctor or it may be obtained interactively from the patient. A preferred embodiment thus provides an interactive profile builder for interactively remotely asking questions of a subject and processing answers of a subject thereby to individualize a respective profile for the subject. A typical way of providing such an interactive profile builder may be as a web-based form. The form is preferably interactive in the sense that questions are arranged in branch format. Only if the subject answers in a certain way on a general question is the patient then asked more detailed questions on the same subject.

The profile builder is thus preferably an Internet text-based form, including an HTML form, an XML form, an STML form, a WAP form and a form based on any other suitable protocol or language. In an alternative embodiment the questions on the form may be spoken. In the event that voice processing is not of sufficient power to deal with spoken replies the subject may be asked to indicate different replies by pressing different keys on the keypad, for example in the event of the subject communicating via a non-digitally-enabled telephone. Whether using text or voice in the interface, there is preferably provided a facility for allowing the user to select the interface language.

In another preferred embodiment, instead of using deltas to alter thresholds in the event of given conditions, rules can be used, as with the combining logic 40 of FIG. 5.

Conditions to which deltas or predetermined modification rules may advantageously be applied include CVA, brain hemorrhage, brain blockage, TIA, Diabetes, Bruit, PMI, or a combination thereof.

A particular measurement that the patient may be able to monitor at home using embodiments of the present invention is blood pressure. Threshold levels in blood pressure measurement would typically be levels that a doctor would wish to modify using deltas or otherwise in the presence of any of the above conditions.

Figure 6:
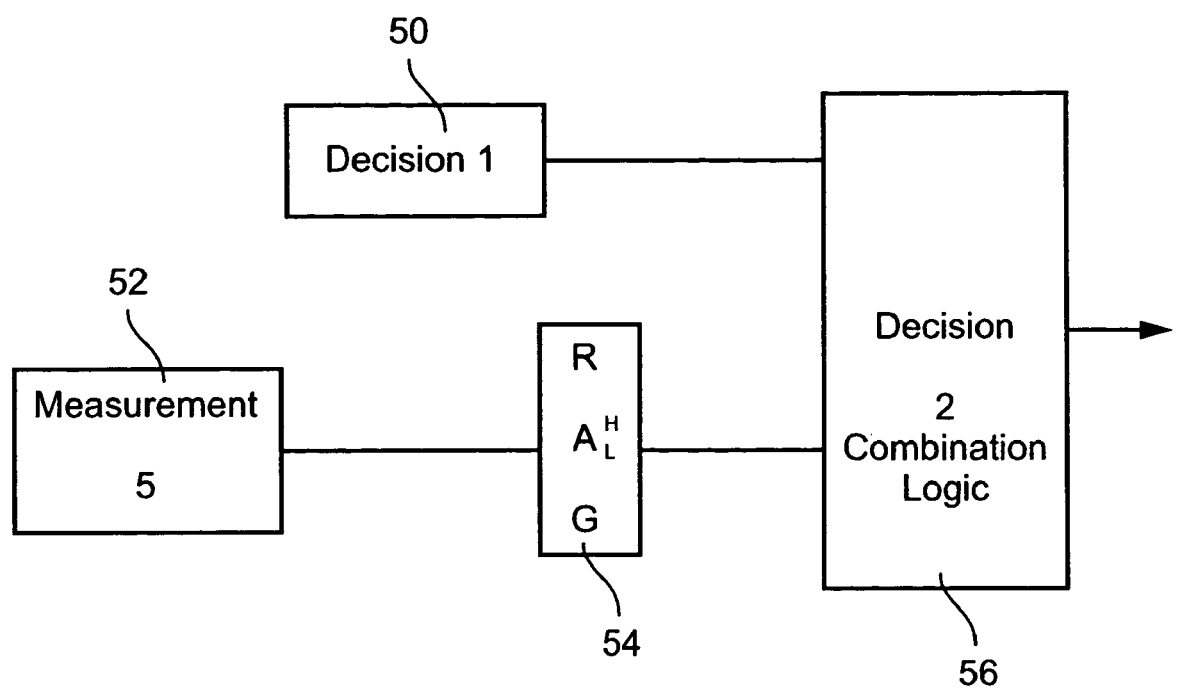
FIG. 6 is a simplified block diagram showing how a first decision may be combined with a new measurement to produce a further output.

Reference is now made to FIG. 6, which is a simplified block diagram showing a further embodiment of the present invention for making recommendations. In the embodiment of FIG. 6, a first recommendation 50 is reached as described in any of the ways described above. A further measurement 52 is then taken from the subject and a status is applied thereto, again as described above at a status assigner unit 54. The first recommendation 50 is then combined with the second measurement using second recommendation combination logic 56. The combination may be achieved by applying a status to the decision 1 output, that is to say regarding certain outputs as red, certain outputs as amber high and so on. Alternatively the combination logic 56 may relate to the individual recommendations themselves. For example a first recommendation to increase dosage combined with an amber high from the second measurement may lead to an overall recommendation "increase dosage plus contact doctor".

In one embodiment the arrangement of FIG. 6 provides a branched test arrangement. The subject is asked to carry out a general test and provides an answer. The result is then given a status. In the event of a red or high amber status a first recommendation is made which is to carry out a further test. The subject is then asked to carry out the further test and the result of the further test is used to make a further decision. For example the subject is initially asked about his overall feeling. If he replies that he feels OK then no tests are carried out. If he replies that he is feeling nauseous then the patient is asked to carry out one or more further tests.

It will be appreciated that a first recommendation can be combined with a single new measurement input or with a plurality of new measurement inputs. Conversely a single new measurement input may be combined with more than one existing recommendation to come to one or more secondary recommendations.

Additionally or alternatively, such a secondary recommendation may be combined with one or more further primary recommendations or one or more other secondary recommendations or one or more new inputs to arrive at a tertiary recommendation. In the same way, fourth, fifth and higher level recommendations may be made.

A branched structure of questioning is advantageous for conciseness. However branching of questions contains a bias towards a foreseen scenario. As an alternative to a branched structure, a further preferred embodiment of the present invention uses a series of lead questions aimed at establishing the presence of a range of conditions. Then instead of a branching structure, rule based logic is used to lead to appropriate follow-up questions. The lead questions and rule based structure may be more helpful than the tree based structure when for example monitoring for heart problems which unexpectedly develops into pneumonia.

Thus, in following a heart patient, the following parameters may be monitored, chest pain, ability to lie down, palpitation, blood pressure, heart rate, weight, and shortness of breath.

Now, if all the answers and the test results are within acceptable limits, except that the patient is showing signs of shortness of breath, then a rule may be set that when shortness of breath is inconsistent with the other results, the system is to start looking for other possibilities. The system may thus be set to ask for information regarding temperature, coughing, sputum (wet cough), whether someone in the family is or has recently been suffering from a respiratory disease or infectious lung disease. It may ask the patient if he is wheezing.

If the patient replies that he has a temperature (vital signs), rash (skin disorder), and arthralgia (skeletal problems), the system may be set via appropriate rules to raise questions about allergy to the current medication and the possibility may be raised of using a new medication. Such questions may include whether the patient has had allergic reactions in the past. Is it the first occurrence of arthralgia? Is there any kind of redness or swelling in the joints? The system is preferably set to take sufficient questions to enable the forming of a view on the patient's condition.

An example of in which rule-based logic outdoes tree-based logic is as follows:

A patient has answered questions that lead to swelling of joints. Subsequently the patient indicates that are problems with urine. The combination of these two answers suggests possible spread of some kind of autoimmune disease, at which point it is appropriate to ask the patient whether his eyes are red, what is the state of his wisdom teeth, and whether there have been changes in the color of his excrement. He may be asked whether his joints feel particularly stuck first thing in the morning. A rule based structure is the best way to get from the initial two questions to the subsidiary questions in the above case simply because the follow-up questions are trivial issues when considering each of the first two questions in isolation, and therefore would be extremely low down on the tree structure for each. The follow-up questions are only of importance once the above answers to both of the initial questions are known in combination.

In a particularly preferred embodiment of the present invention, a tree based structure is used initially to ask questions about the condition being monitored. Then an additional set of lead questions is asked and used together with initial answers in rule based logic to determine whether anything unexpected is happening.

Returning to the heart patient, if the patient is able to supply good, meaning clear, answers to the above set of questions, then—it is possible to proceed. If the answers are ambiguous then either a tree or a rule-based structure may be used to ask the original question in a different way, for example a question about stiffness of joints can be rephrased by asking if the patient has added, or felt the need to add, more pillows at night.

Figure 7:
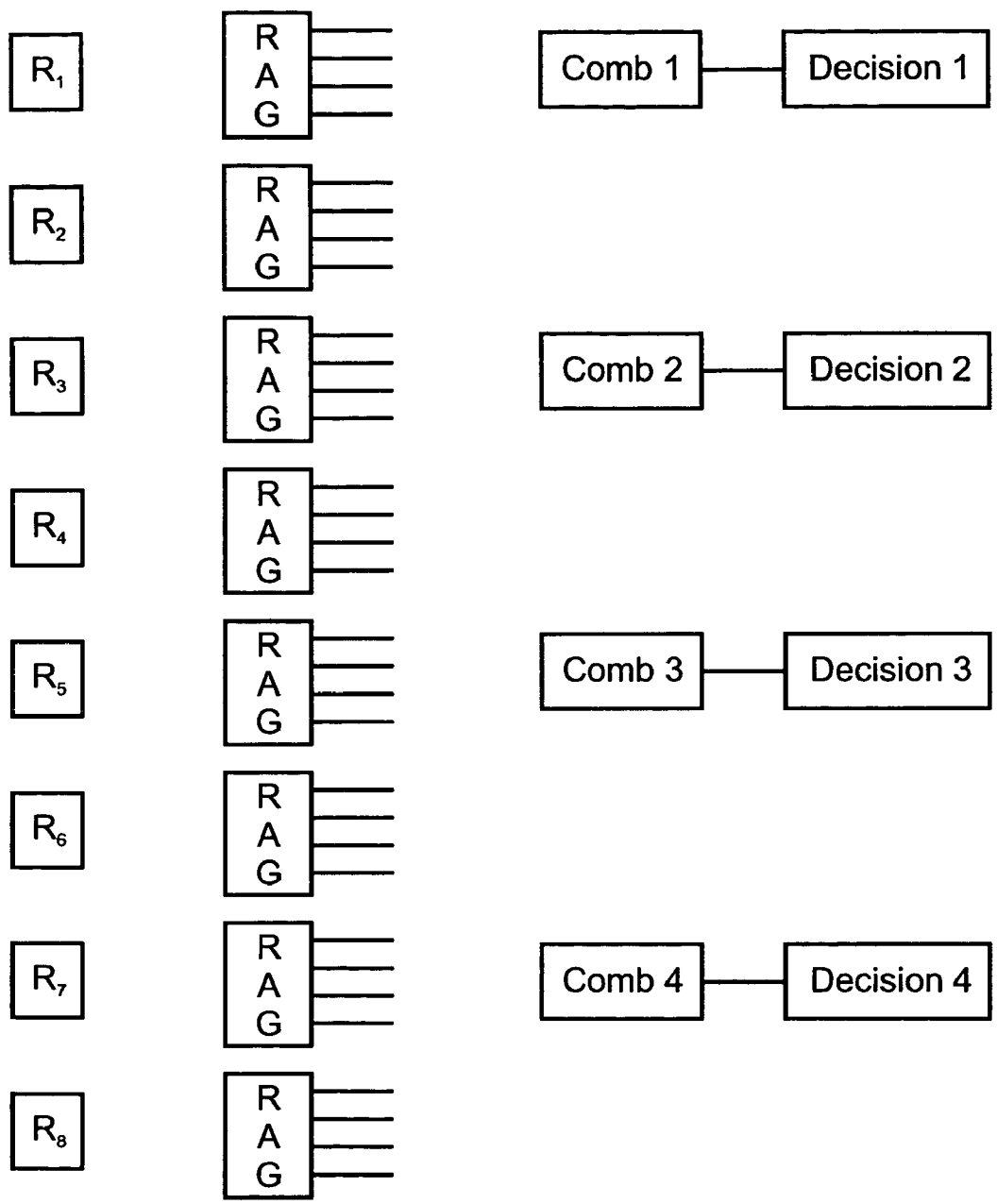
FIG. 7 is a simplified block diagram showing a single set of inputs being combined in different ways to lead to different decisions.

Reference is now made to FIG. 7, which is a simplified block diagram showing how a set of input measurements may each be combined in different ways using different combination logic and different rules to produce different output recommendations 1 to 4. In the figure, inputs R1 to R8 are each assigned status levels as before and then combined in four different sets of combination logic to yield different output recommendations. Thus a given set of measurements combined in different ways may lead to a series of different recommendations such that several different recommendations are based on substantially the same measurement set. Some of the output recommendations may use all of the inputs and some may use fewer than all of the inputs.

Figure 8:
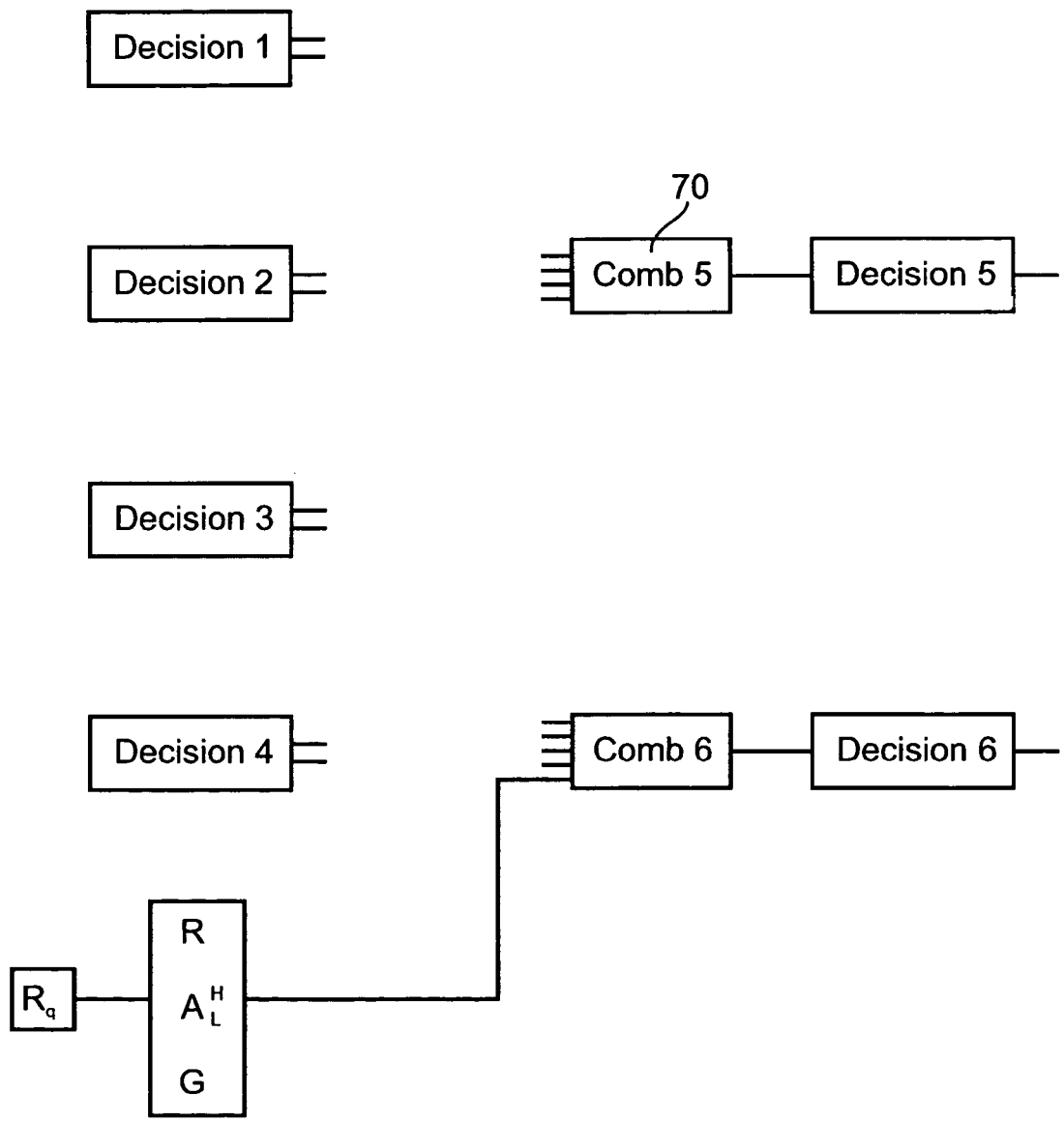
FIG. 8 is a simplified block diagram showing multiple first level decisions being combined to form a second level decision and also being combined with a new input to form another second level decision.

Reference is now made to FIG. 8, which is a simplified block diagram illustrating a layout for producing secondary recommendations. In FIG. 8, recommendations 1 to 4 of FIG. 7 are combined, using combination logic 70 to produce a secondary recommendation 5. Secondary recommendation 5 is thus produced, using rules, based on the combinations of recommendations 1 to 4. Recommendation 6 is produced by combination logic 72 using recommendations 1 to 4 and a new input R9.

Reference is now made to FIG. 9, which is a simplified schematic diagram showing a login screen for a web-browser implementation of the present invention. The user is simply asked to give his name and a password or pin number or the like in order to identify the patient and associate the patient with the correct profile.

Figure 11:
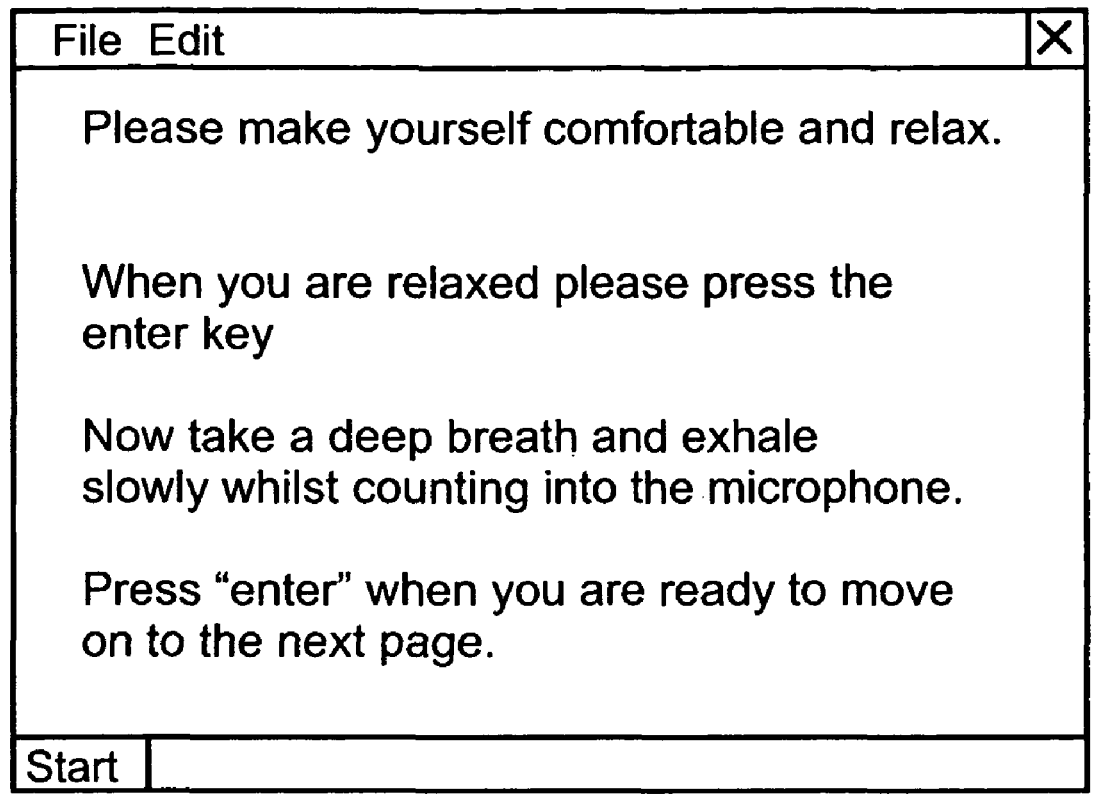

It is noted that whilst FIGS. 9-11 show connection over a web browser, the same information as carried by the web browser screens can be conveyed in voice form over a telephone connection, the patient making use of DTMF tones to provide his replies.

In either case a password is preferably used to assure the patient of confidentiality and to assure the doctor that the correct patient is answering. Preferably an alternative communication path is used to inform the patient of his password. Thus if the patient connects via a regular telephone, the password may be sent via beeper or mobile telephone.

Reference is now made to FIG. 10, which is a simplified schematic diagram showing an introductory screen, again for a web browser implementation of the present invention. The screen asks the user to answer some simple questions such as overall feeling and whether a patient has taken his pills.

Reference is now made to FIG. 11, which is a simplified diagram showing how the dyspnea monitoring test may be implemented in a web browser implementation of the present invention. The user is invited to relax and then take a deep breath. He is then asked to exhale slowly whilst counting into the microphone.

The interface 20, in the web implementation, may thus present to the subject a personalized web page which asks the subject questions relevant to his condition and is able to process the data in a way that is responsive to his current condition and to his case history. Any recommendation made is readily analyzable since inputs are coded in such a way as to be user friendly. Thus the system avoids the common criticism applied to expert systems of being black boxes and it being impossible to find out the reasons for the recommendation or to be sure that it has taken a given factor into account.

The monitoring arrangement of the above embodiments gives a patient an opportunity to answer routine questions before going to see a doctor. Particularly in the case of specialist doctors it can be advantageous for the doctor to have an idea of the situation or a status update before seeing the patient. Thus a patient who has been using an embodiment of the present invention for regular tests etc. may receive a telephone call or an additional web form to answer routine questions before seeing the doctor.

Routine monitoring of the kind described hereinabove is particularly useful in cases of chronic illness, and for post-encounter or post operation follow-up, also after an invasive test or examination, or following chemotherapy, or giving birth. Examples of post encounter include a visit to the doctor, checkup of any kind e.g. laboratory X-ray, any kind of treatment, ambulatory treatment, any kind of emergency treatment, and all kinds of hospitalization with or without invasive procedures. The system is useful in warning about post-hospitalization infection or relapses or impending bouts of pneumonia. In particular, one of the reasons that pneumonia is so often fatal is that it is often diagnosed too late for drug treatments to be effective.

The system may be used prior to an operation, or prior to any ambulatory treatment to provide to the patient an interactive pre-operation questionnaire which may be used to build a user profile as described above. The profile may then be used as described above to modify thresholds.

Again, as described above, questions may be arranged in a tree and branch format so that in the pre-encounter or pre-operation questionnaire, only sub-questions that appear to be relevant based on earlier questions are asked. Following the operation or encounter, a post encounter questionnaire may then be built up by branching in accordance with answers given in the pre-operation questionnaire.

In use, the present embodiments are preferably arranged so that telephone call charges are clearly distinguishable as being related to medical care. The calls are preferably charged to the hospital account or are routed through a specific exchange that takes only calls relating to patient monitoring so that it is intrinsically clear that all calls routed through the exchange are patient care related calls. More particularly, in the US medical system a hospital or like medical institution can assign costs to a number of reports in order to obtain reimbursement from the various medical service providers. Costs that relate to patients whilst hospitalized are assigned to what is known as the medical report and are reimbursed to the hospital by the medical providers. The issue with telemedicine is that the patient is not hospitalized so that despite the fact that the costs are very much lower, the hospital cannot charge the costs to the medical report and hope for reimbursement. A further point is that patient expectation, especially of customers of medical insurance, is of free delivery at point of service. Thus the hospital is obliged to provide its service using such features as 1-800 free call services. These increase the cost to the hospital.

As well as telemedicine itself, there is also what is known as EMR, standing for electronic medical record. The patient fills in medical forms, questionnaires etc. online, and it is desirable to fill in such forms from home. Thus valuable time with the physician can be saved and pointless visits can be filtered out. Likewise patients uncertain about whether it is necessary to visit a physician can answer a questionnaire and find out whether they should visit the physician or not, thus improving the likelihood that necessary visits are actually made. Also, patients can be given pre-visit instructions, asked to sign consent forms, and given post hospitalization instructions, post-invasive procedure instructions and the like.

The telemedicine or EMR systems can make use of web forms, email, SMS messages over the cellular network and the like, as well as voice based interactive systems over a regular telephone. Any of these methods and others can be used for giving patients instructions, inviting them for a visit etc.

Figure 12:
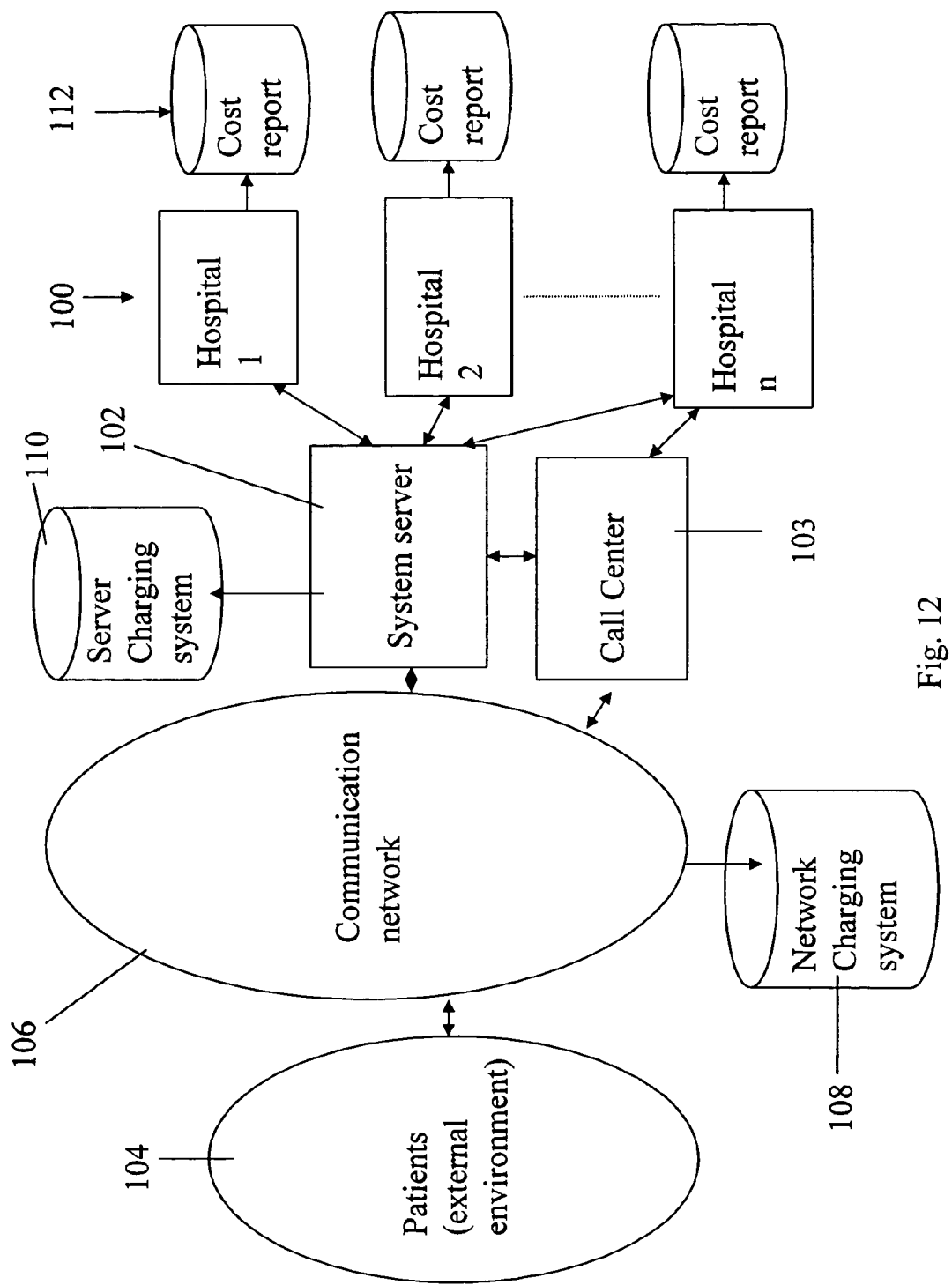
FIG. 12 is a simplified diagram illustrating an infrastructure for providing a telemedicine or patient questionnaire or patient information service, according to a preferred embodiment of the present invention.

Reference is now made to FIG. 12, which is a simplified diagram illustrating a system for remote interaction with patients. A series of hospitals 100.1 ... 100.*n* are connected to a server or server-based system 102 which manages an interactive system. The server 102 includes servers and communications equipment for communicating with remotely located patients 104 over a communication network 106.

In addition to the server there may be provided a manned called center 103, where operators are able to direct calls, or pass on or answer queries. A manned call center is relatively expensive and so making the maximal use of the automated server is cost effective. However, certain types of query are difficult to deal with automatically and thus a hybrid system having both a server and a call center maximizes the advantages of both.

The server system, or the hybrid, are able to provide services with medical content, including diagnosis and advice, and collecting medical (health) data, services in terms of arranging visits and consultations, and sales and marketing.

In one embodiment the call center is replaced by a direct connection to the hospital, so that urgent or complex queries can be dealt with by medical professionals.

In another embodiment the server is able to deal with certain issues on its own, certain other issues are forwarded to the call center and certain issues are forwarded to the hospital.

The communication network 106 may be the public switched telephone network, or the Internet, or the cellular telephone network or the cable television network or a combination of these or any other suitable communication infrastructure. The communication network has a charging infrastructure 108 for charging for the use of the system. The PSTN or cellular telephony networks generally charge the calling party for connection time. A system of this nature may often be set up not to charge the patients even if they initiate the calls, using free (to calling party) phone numbers such the 1-800 service. On the Internet, users are generally charged monthly fees. Likewise the call center and the server most likely have a charging infrastructure 110 for charging their clients, namely the hospitals, for use of its services. The hospitals have an account known as a medical report, through which they receive reimbursement for the running costs of a patient in hospital, but telemedicine cannot be covered by such a system since the patient is not in the hospital. Thus instead the costs of running the system, including as necessary both the costs of the communication network and the cost of the call center is included on the hospital's cost report 112, which covers infrastructure costs to the hospital and which is also reimbursed by the medical providers. As a result the telemedicine service becomes cost neutral to the hospital but the medical providers can charge their customers for the telemedicine services. The cost report may be known by different names under different accountancy systems but is the accounting entity which includes communications costs or telephone bills.

Figure 13:
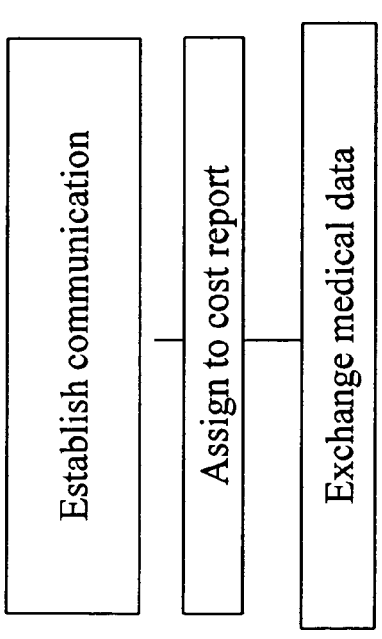
FIG. 13 is a simplified flow chart illustrating basic use of the infrastructure of FIG. 12.

Reference is now made to FIG. 13, which is a simplified flow chart illustrating use of the system of FIG. 12. In FIG. 13 the system establishes communication between a patient and the hospital or call center. The network costs are assigned to the cost report and medical (health) data is exchanged.

Figure 14:
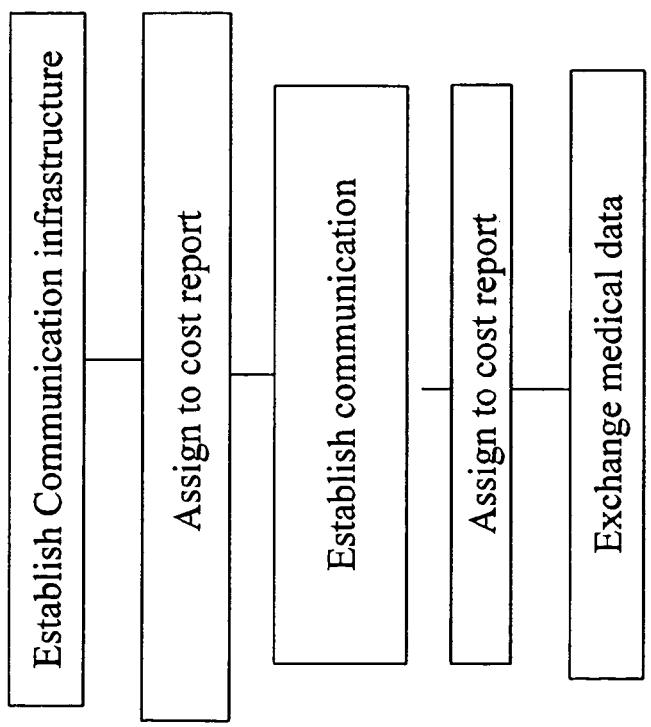
FIG. 14 is a simplified flow chart adding assignment of infrastructure costs to the flow of FIG. 13.

Reference is now made to FIG. 14, which is a simplified flow chart illustrating an extension of the use of the system of FIG. 12. In FIG. 14 the communication infrastructure, such as the call center, is set up. The costs of the call center are applied to the cost report, and then the subsequent costs of the communications themselves are also applied to the cost report.

Figure 15:
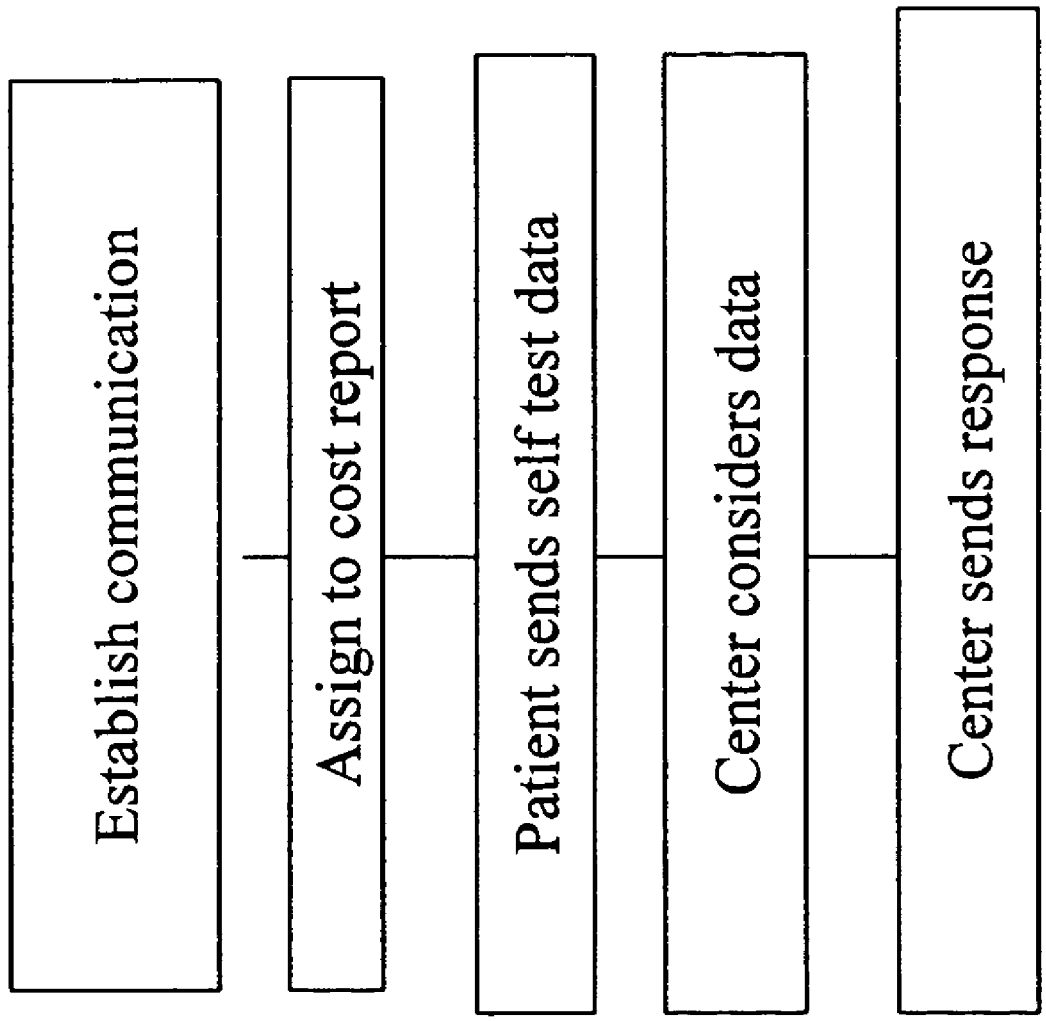
FIG. 15 is a simplified diagram illustrating a telemedicine procedure using the infrastructure of FIG. 12.

Reference is now made to FIG. 15, which shows the process of a patient carrying out a self-administered test using the present embodiments. In FIG. 15 the communication is established and the costs are assigned to the cost report. The patient then enters the results of the self-administered tests which are considered and an acknowledgement or other reaction is received by the patient in response. It is noted that the raw test information can also be sent via the communication channel as with the dyspnea test described hereinabove.

Reference is now made to FIG. 16, which is a simplified flow chart illustrating the process of EMR using the system of the present invention. In EMR, the call is placed and the cost is assigned to the cost report. Then the system determines that certain information is needed by the patient or by the system from the patient. The patient is sent the necessary information or the necessary forms or questionnaires. The patient signs the forms or fills in the questionnaires or reads and acknowledges the information. In one embodiment the user is asked questions about the information he has been given in order to ascertain that he has understood the information.

The center considers the patient's responses etc. and sends the patient further advice, instructions or information as necessary.

Reference is now made to FIG. 17a which is a simplified block diagram illustrating a first system for remote medical interaction with a patient, according to a preferred embodiment of the present invention.

An alternative or additional system 1700, according to a preferred embodiment of the present invention includes a tester, or a sensor 1710, used for acquiring medical (health) data from a patient. For example the tester, or a sensor may be used by the patient 1701 to self administer a blood pressure/heart rate examination, or a respiratory examination as described herein above.

Preferably, the tester 1710 comprises a processor. More preferably, the tester 1710 is also programmable.

The system 1700 further includes a personal transmitter 1720 which is connected to the tester, or a sensor 1710, configured to automatically transmit the medical (health) data which is acquired using the tester, or a sensor, say during a self administered test as described hereinabove. Optionally, the transmission is carried out wirelessly, using any of currently used local wireless communication means 1750, including but not limited to: Worldwide Interoperability for Microwave access (WiMax) networks—Broadband wireless networks that are based on the IEEE 802.16 standard, Bluetooth—Short range radio links in the 2.4 GHZ frequency range, WiFi—wireless local area networks (WLAN) that use specifications conforming to IEEE 802.11b, standard radio channels, or any other radio wave channel.

With wireless transmission of medical (health) data, the patient's monitoring is no longer limited to a stationary mode in which a patient has to be present in a specific station where the testing or sending of medical (health) data may take place. That is to say that with wireless transmission the patient may be continuously monitored, in real time, as he walks around, drives, works, etc.

For example, an ischemic disease patient may be provided with the tester, or a sensor (medical sensor) 1710 and the personal transmitter (or communicator) 1720 which wirelessly and continuously transmits cardiac medical (health) data to a medical center, say through a local communicator 1730 as described herein below.

The tester may include a sensor, a medical sensor, or any other device for measuring a health condition in a patient. The tester may collect medical (health) data, including any kind of measurable or verbal information from human being. Optionally, the sensor or the tester may include processing ability. More preferably, the sensor or tester may be programmable.

The personal communicator may be, but is not limited to a general purpose computer, or any other programmable device. Preferably, the local communicator is locally or remotely programmable. More preferably, the local communicator further includes a software downloading capability.

In one example, the medical (health) data includes measured ECG parameters.

The continuous monitoring of the ischemic patient in real time facilitates immediate detection of an ischemic emergency condition such as a heart attack or a state of severe arrhythmia, say according to a rapidly elevating blood pressure, an accelerated heart rate, ECG R-R interval, P-R interval, Q-S-interval, Q-T interval, and the height of the S-T segment as compared with the height of the P-Q segment and the T-P segment.

The real time delivery of medical (health) data to the medical center may prove life saving as the sooner a stressed patient is treated, to more likely he is to survive an heart attack or any other medical emergency situation.

In another example, an epileptic patient may be continuously monitored for his brain electric signals thus facilitating an immediate detection of a seizure. The immediate detection of the seizure may prove life saving, say when the monitored patient experiences the seizure when driving etc. Preferably, the system further includes a local communicator 1730, such as a locally deployed communication server which forwards the medical (health) data to a remote receiver 1740.

The local communicator may be, but is not limited to a general purpose computer, or any other programmable device.

More preferably, the local communicator 1730 is further configured to process the medical (health) data prior to forwarding it to the remote receiver. For example, the local communicator 1730 may be a local computer which is programmed to filter out noise or any other irrelevant data from the medical (health) data prior to forwarding the noise-free medical (health) data to the remote receiver 1740.

Optionally, the local communicator 1730 is a third generation (3 GL) mobile phone installed with a dedicated application, for receiving the medical (health) data from the personal transmitter 1720, and forwarding the medical (health) data to remote receiver 1740, as described in greater detail hereinabove.

The remote receiver 1740 may be a server or server-based system which manages an interactive system, deployed in the premises of a hospital or any other medical services provider, as described in greater detail herein above. The remote receiver includes servers and communications equipment for communicating with remotely located patients over a communication network.

Optionally, the network used for the remote communication with the patient may be but is not limited to a traditional system telephony network or any other wide area communication network 1770.

Optionally, the medical (health) data may be processed or analyzed by the tester, or a sensor 1710, by the personal communicator 1720, by the local communicator 1730, by the remote receiver 1740, or by any combination thereof.

Optionally, the processing of the medical (health) data may include automatically generating recommendations. The generated recommendations may be based, or the acquired medical (health) data as well as on previously stored medical (health) data of the patient.

In particular, respiratory system medical (health) data, generated through a self administered patient examination, may be processed and analyzed for an early detection of respiratory problems, as described in greater detail hereinabove.

For example, the tester, or a sensor 1710, the local communicator 1730, or the remote receiver 1740 may include a breathing interval beginning determinator, for determining a beginning of a breathing interval, a breathing interval end determinator, for determining a termination of the breathing interval, a timer associated with the breathing interval beginning determinator and the breathing interval end determinator to measure a time interval between the beginning and the determination, and a processor operable with the timer to assign levels of importance to the measured time interval.

Optionally, the processor may be further configured to compare the time interval with one or more predefined threshold(s) for assigning a level of importance to the measured interval, say for indicating the severity of a respiratory condition of the patient, as described in greater detail hereinabove.

Figure 17B:
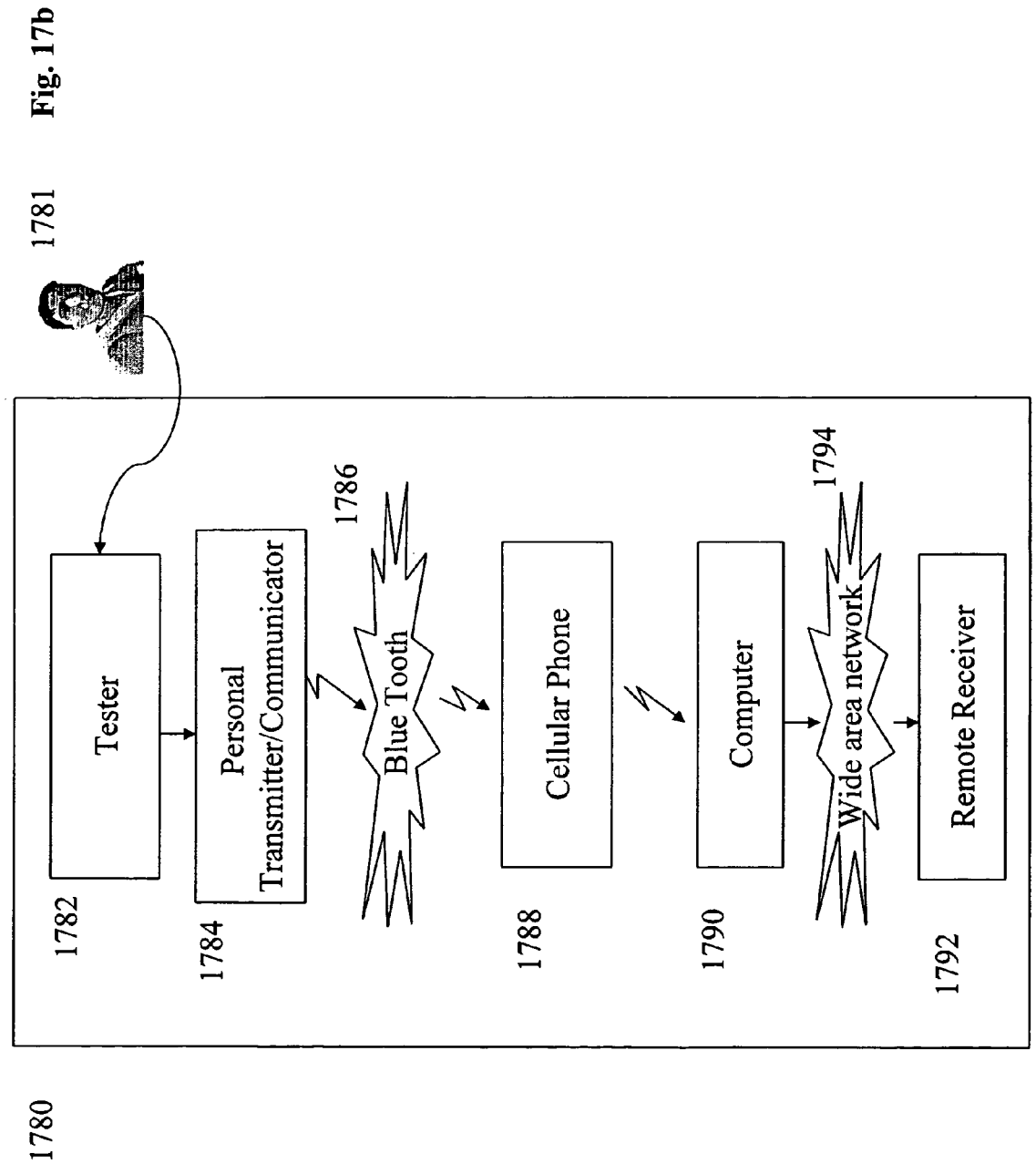
FIG. 17*b* is a simplified block diagram illustrating a second system for remote medical interaction with a patient, according to a preferred embodiment of the present invention.

Reference is now made to FIG. 17*b* which is a simplified block diagram illustrating a first system for remote medical interaction with a patient, according to a preferred embodiment of the present invention.

An alternative or additional system 1780, according to a preferred embodiment of the present invention includes a tester, or a sensor 1782, used for acquiring medical (health) data from a patient 1781. For example the tester, or a sensor may be used by the patient 1781 to self administer a blood pressure/heart rate examination, or a respiratory examination as described herein above.

The system 1780 further includes a personal transmitter 1784 which is connected to the tester, or a sensor 1782 and configured to automatically transmit the medical (health) data acquired by the tester, or a sensor, say during a self administered test as described hereinabove. The medical information is transmitted wirelessly, using a Bluetooth link 1786—a short range radio links in the 2.4 GHZ frequency range, to a Bluetooth compatible mobile phone 1788.

The Bluetooth compatible phone, in turn, forwards the medical (health) data to a computer 1790 implementing a local communicator, as described hereinabove with regards to FIG. 17*a*.

The computer 1790 is preprogrammed to forward the medical (health) data to a remote receiver 1792, say via a wide area communication network 1794, as described hereinabove, as described in greater detail hereinabove.

Preferably, the computer is further preprogrammed to process the medical (health) data prior to forwarding the medical (health) data to the remote receiver 1792, say by filtering out noise or other irrelevant data, as discussed hereinabove.

Reference is now made to FIG. 18 which is a flowchart illustrating a method for remote medical interaction with a patient, according to a preferred embodiment of the present invention.

In a method according to a preferred embodiment of the present invention, medical (health) data is acquired 1810 from a monitored patient, say by a tester, or a sensor 1710 as described hereinabove.

Then the medical (health) data is transmitted 1820 automatically and wirelessly via a local wireless communication link, say using a personal communicator 1720, as described in greater derail hereinabove.

Finally, the transmitted medical (health) data is forwarded, say using a local communicator 1720 communicating with a remote receiver 1740, as illustrated and described in greater detail hereinabove.

It is expected that during the life of this patent many relevant devices and systems will be developed and the scope of the terms herein, particularly of the terms "WiFi", "WiMax", "Bluetooth", and "radio wave", is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for remote medical interaction, comprising:
   sending and receiving medical data over a wireless communication link using a wireless device of a local communicator;
   determining, at the local communicator, a beginning of a breathing interval using at least a portion of the medical data;
   determining, at the local communicator, an end of the breathing interval using the at least a portion of the medical data;
   determining, at a timer of the local communicator, a time interval between the beginning of the breathing interval and the end of the breathing interval;
   assigning, at a processor of the local communicator, a level of importance out of a plurality of levels of importance to the time interval;
   determining, at the processor of the local communicator, a recommendation based on the level of importance; and
   sending at least the recommendation over the wireless communication link.

2. The method of claim 1, wherein the medical data comprises data about a heart of a patient.

3. The method of claim 1, wherein the medical data comprises blood pressure data.

4. The method of claim 1, wherein assigning the level of importance out of the plurality of levels of importance to the time interval comprises:
   determining at least one time-interval threshold; and
   determining the level of importance based on the at least one time-interval threshold.

5. The method of claim 1, wherein assigning the level of importance comprises comparing the time interval with one or more predefined thresholds.

6. The method of claim 1, further comprising:
   sending a request based on the recommendation over the wireless communication link.

7. The method of claim 1, further comprising:
   determining a medical history of a patient; and wherein determining the recommendation based on the level of importance comprises:

determining the recommendation based on the level of importance and the medical history.

8. The method of claim 1, further comprising:
determining an alert threshold;
responsive to the level of importance equaling or exceeding the alert threshold, communicating an alert.

9. The method of claim 8, wherein communicating the alert comprises:
communicating the alert via a first communication technology in response to determining the level of importance equals a first level of importance, wherein the first level of importance equals or exceeds the alert threshold; and
communicating the alert via a second communication technology in response to determining the level of importance equals a second level of importance, wherein the second level of importance exceeds the first level of importance.

10. A local communicator, comprising:
a wireless device, configured to send and receive medical data over a wireless communication link;
a breathing interval beginning determinator, configured to determine a beginning of a breathing interval using at least a portion of the medical data;
a breathing interval end determinator, configured to determine an end of the breathing interval using the at least a portion of the medical data;
a timer, configured to measure a time interval between the beginning of the breathing interval and the end of the breathing interval; and
a processor, configured to:
assign a level of importance out of a plurality of levels of importance to the time interval;
determine a recommendation based on the level of importance; and
send at least the recommendation over the wireless communication link.

11. The local communicator of claim 10, wherein the plurality of levels of importance comprises a red level, an amber level, and a green level.

12. The local communicator of claim 10, wherein the processor is configured to assign the level of importance by comparing the time interval with one or more predefined thresholds.

13. The local communicator of claim 10, wherein the local communicator further comprises a software downloading capability.

14. The local communicator of claim 10, wherein the processor is further configured to:
determine one or more rules associating the plurality of levels of importance and a range of output recommendations;
select the recommendation from the range of output recommendations applying the one or more rules to the level of importance.

15. The local communicator of claim 10, wherein the processor is further configured to:
send a request based on the recommendation over the wireless communication link.

16. The local communicator of claim 10, wherein the processor is further configured to determine a medical history of a patient; and
wherein the processor is configured to determine the recommendation by:
determining the recommendation based on the level of importance and the medical history.

17. The local communicator of claim 10, wherein the processor is further configured to:
determine a first recommendation based on the level of importance;
receive a measurement over the wireless communication link;
determine a second recommendation by combining the first recommendation with the measurement; and
send the second recommendation over the wireless communication link.

18. The local communicator of claim 10, further comprising an audio interface, and wherein the processor is further configured to output one or more questions related to the recommendation via the audio interface.

19. The local communicator of claim 10, wherein the processor configured to send at least the recommendation over the wireless communication link is further configured to send the medical data over the wireless communication link.

20. The local communicator of claim 16, wherein the processor is configured to determine the recommendation based on the level of importance and the medical history by:
determining one or more thresholds;
determining a set of deltas;
applying the set of deltas to the one or more thresholds; and
determining the recommendation based on the applied one or more thresholds.

21. The local communicator of claim 20, wherein the processor is configured to determine the set of deltas by:
determining a condition based on the medical history; and
determine the set of deltas based on the condition.

22. An apparatus, comprising:
means for sending and receiving medical data;
means for determining a beginning of a breathing interval using at least a portion of the medical data;
means for determining an end of the breathing interval using the at least a portion of the medical data;
means for determining a time interval between the beginning of the breathing interval and the end of the breathing interval; and
means for processing, configured for:
assigning a level of importance out of a plurality of levels of importance to the time interval;
determining a recommendation based on the level of importance; and
sending at least the recommendation.

23. The apparatus of claim 22, wherein assigning the level of importance to the time interval comprises:
determining at least one time-interval threshold; and
determining the level of importance based on the at least one time-interval threshold.

24. The apparatus of claim 22, further comprising means for outputting the recommendation.

25. The apparatus of claim 22, wherein the means for processing are further configured for sending a request based on the recommendation.

26. The apparatus of claim 22, wherein the means for processing are further configured for:
determining an alert threshold;
communicating an alert, in response to determining the level of importance equals or exceeds the alert threshold.

27. The apparatus of claim 22, wherein the plurality of levels of importance comprises a red level, an amber level, and a green level.

28. The apparatus of claim 22, further comprising means for determining a medical history of a patient; and wherein determining the recommendation based on the level of importance comprises determining the recommendation based on the level of importance and the medical history.

29. The apparatus of claim 28, wherein determining the recommendation based on the level of importance and the medical history comprises:
   determining one or more thresholds;
   determining a set of deltas, comprising:
   determining a condition based on the medical history;
   determining the set of deltas based on the condition;
   applying the set of deltas to the one or more thresholds; and
   determining the recommendation based on the applied thresholds.

* * * * *

UNITED STATES PATENT AND TRADEMARK OFFICE
CERTIFICATE OF CORRECTION

PATENT NO. : 8,043,224 B2  Page 1 of 1
APPLICATION NO. : 11/390301
DATED : October 25, 2011
INVENTOR(S) : Sarel It is certified that error appears in the above-identified patent and that said Letters Patent is hereby corrected as shown below:

Title Page 2, item (56), under "Other Publications", in Column 2, Line 1, delete "Microsoft Microsoft" and insert -- Microsoft --.

Signed and Sealed this
Nineteenth Day of June, 2012

David J. Kappos
*Director of the United States Patent and Trademark Office*